United States Patent
Agnew et al.

(10) Patent No.: US 10,632,133 B2
(45) Date of Patent: Apr. 28, 2020

(54) ANTI-VIRAL AZIDE CONTAINING COMPOUNDS

(71) Applicants: Life Technologies Corporation, Carlsbad, CA (US); The Johns Hopkins University, Baltimore, MD (US)

(72) Inventors: Brian Agnew, Eugene, OR (US); David Graham, Baltimore, MD (US); Upinder Singh, Eugene, OR (US); Scott Grecian, Fall Creek, OR (US)

(73) Assignees: THE JOHNS HOPKINS UNIVERSITY, Baltimore, MD (US); LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/834,639

(22) Filed: Dec. 7, 2017

(65) Prior Publication Data

US 2018/0092932 A1    Apr. 5, 2018

Related U.S. Application Data

(62) Division of application No. 14/831,220, filed on Aug. 20, 2015, now Pat. No. 9,855,287, which is a division of application No. 13/192,959, filed on Jul. 28, 2011, now Pat. No. 9,144,575.

(60) Provisional application No. 61/368,565, filed on Jul. 28, 2010.

(51) Int. Cl.
| | | |
|---|---|---|
| *A61K 31/655* | (2006.01) | |
| *A61K 31/7024* | (2006.01) | |
| *A61K 45/06* | (2006.01) | |
| *A61K 31/7088* | (2006.01) | |
| *A61K 38/21* | (2006.01) | |

(52) U.S. Cl.
CPC ........ *A61K 31/655* (2013.01); *A61K 31/7024* (2013.01); *A61K 31/7088* (2013.01); *A61K 38/212* (2013.01); *A61K 38/215* (2013.01); *A61K 45/06* (2013.01)

(58) Field of Classification Search
None
See application file for complete search history.

(56) References Cited

U.S. PATENT DOCUMENTS

| | | |
|---|---|---|
| 4,427,649 A | 1/1984 | Dingle et al. |
| 4,522,811 A | 6/1985 | Eppstein et al. |
| 4,839,175 A | 6/1989 | Guo et al. |
| 5,049,388 A | 9/1991 | Knight et al. |
| 5,073,571 A | 12/1991 | Heuckeroth |
| 5,141,674 A | 8/1992 | Leigh |
| 5,338,858 A | 8/1994 | Devadas et al. |
| 5,397,701 A | 3/1995 | Devadas et al. |
| 5,422,120 A | 6/1995 | Kim |
| 5,498,420 A | 3/1996 | Mentrup et al. |
| 5,569,464 A | 10/1996 | Endo et al. |
| 5,998,476 A | 12/1999 | Sleigh |
| 6,228,393 B1 | 5/2001 | DiCosmo et al. |
| 6,365,628 B1 | 4/2002 | Berge |
| 2005/0106627 A1 | 5/2005 | Zhao et al. |
| 2005/0112199 A1 | 5/2005 | Padval et al. |
| 2005/0222427 A1 | 10/2005 | Sharpless et al. |
| 2007/0190597 A1 | 8/2007 | Agnew et al. |
| 2007/0249014 A1 | 10/2007 | Agnew et al. |
| 2008/0267878 A1 | 10/2008 | Robillard et al. |
| 2012/0028244 A1 | 2/2012 | Agnew et al. |
| 2012/0028335 A1 | 2/2012 | Agnew et al. |
| 2013/0089884 A1 | 4/2013 | Agnew et al. |
| 2013/0209364 A1 | 8/2013 | Agnew et al. |
| 2013/0209550 A1 | 8/2013 | Agnew et al. |

FOREIGN PATENT DOCUMENTS

| | | |
|---|---|---|
| EP | 0249561 | 12/1987 |
| EP | 0480901 | 4/1992 |
| WO | 87/01586 | 3/1987 |
| WO | 88/01862 | 3/1988 |
| WO | 98/00111 | 1/1998 |
| WO | 98/58629 | 12/1998 |
| WO | 00/38681 | 7/2000 |

(Continued)

OTHER PUBLICATIONS

Prescher, Jennifer A. et al, "Chemical remodellin gof cell surfaces in living animals." Nature (2004) 430 p. 873-879.*
The package insert for Retrovir® (1996).*
Baker, Robert H. and Martin, William B., "A side reacton in the williamson synthesis II." J. Org. Chem. (1960) 25(9) p. 1496-1498.*
"Click-iT Metabolic Labeling Reagents for Proteins", Molecular Probes, 2009, pp. 1-10.
Agard, N et al., "A Strain-Promoted [3+2]Azide-Alkyne Cycloaddition for Covalent Modification of Biomolecules in Living Systems", J. Am. Chem Soc, vol. 126(46), 2004, pp. 15046-15047.

(Continued)

*Primary Examiner* — Fred H Reynolds
(74) *Attorney, Agent, or Firm* — MH2 TECHNOLOGY LAW GROUP, LLP

(57) ABSTRACT

Methods of using azide-modified biomolecules, such as fatty acids, carbohydrates and lipids, to treat a plant, an insect or an animal infected with a virus or to inhibit infectivity of a virus, such as the human immunodeficiency virus, are provided. Also provided are methods of labeling a virus, such as human immunodeficiency virus, with an azide-modified biomolecule, such as a fatty acid, a carbohydrate, or an isoprenoid lipid. Also, provided are methods of tracking a virus in vivo, with an azide-modified biomolecule, such as a fatty acid, a carbohydrate, or an isoprenoid lipid. The azide-modified biomolecules may be combined with a pharmaceutically acceptable excipient to produce a pharmaceutical composition, optionally containing another anti-viral agent and/or a delivery agent, such as a liposome.

8 Claims, 5 Drawing Sheets

(56) References Cited

FOREIGN PATENT DOCUMENTS

| WO | 03/101972 | 12/2003 |
|---|---|---|
| WO | 03/105805 | 12/2003 |
| WO | 05/39533 | 5/2005 |
| WO | 2005/093049 A1 | 10/2005 |
| WO | 08/29281 | 3/2008 |
| WO | 2009/067663 | 5/2009 |

OTHER PUBLICATIONS

Banerjee, Patricia et al., "Chemoselective Modifiation of Viral Proteins Bearing Metabolically Introducted "Clickble" Amino Acids and Sugars", Bioconjugatin Protocals; Strategies and Methods, Methods in Molecular Biology, 751, Chapter 5, 2011, pp. 55-56.
Banerjee, Partha et al., "Unnatural Amino Acid Incorporation onto Advenoviral Coat Proteins Facilitates Chemoseletive Modification and Retargeting of Ad5 vectors", American Society for Microbiology, 2011, pp. 1-34.
Bertozzi et al., "A Strain-Promoted [3+2] Azide-Alkyne Cycloaddition for Covalent Modification of Biomolecules in Living Systems", J. Am. Chem. Soc., 126, 2004, pp. 15046-15047.
Bezombes, C. et al., "Implication of raft microdomains in drug induced apoptosis", Curr Med Chem Anti-Canc Agents, vol. 3, 2003, pp. 263-270.
Boasso, A. et al., "How does indoleamine 2, 3-dioxygenase contribute to HIV-mediated immune dysregulation", Curr Drug Metab, vol. 8, 2007, pp. 217-223.
Bossart-Whitaker, et al., "Three-dimensional Structure of Influenza A 9 Neuraminidase and its Complex with the Inhibitor 2-Deoxy 2,3-Dehydro-N-Acetyl Neuraminic Acid", J. Mol. Biol., vol. 232, 1993, pp. 1069-1083.
Campbell, S. M. et al., "Virion-associated cholesterol is critical for the maintenance of HIV-1 structure and infectivity", Aids, vol. 16, pp. 2253-2261.
Campbell, Shahan et al., "The Raft-Promoting Property of Virion-Associated Cholesterol, but Not the Presence of Virion-Associated Brij 98 rafts, is a Determinant of Human Immunodeficiency Virus Type 1 Infectivity", Journal of Virology, 78(19), 2005, pp. 10556-10565.
Capila, Ishan et al., "Heparin-Protein Interactions", Angewandte Chemie International Edition in English, vol. 41, 2002, pp. 390-412.
Chang, Pamela V. et al., "Copper-free click chemistry in living animals", Proc Nat Aced Sci, vol. 107, No. 5, 2010, 1821-1826.
Charron, Guillaume et al., "Robust Fluorescent Detection of Protein fatty-Acylation iwth Chemical Reports", J. Am. Chem. Soc. 131, 2009, pp. 4967-4975.
Chen M.F. et al., "HIV gp120 V(1)V(2) and C(2)-V(3) domains glycoprotein compatibility is required for viral replication", Virus Res., vol. 79, 2001, pp. 91-101.
De Clercq, Erik, "The bicyclam AMD3100 story", Nature Reviews Drug Discovery, vol. 2, 2003, pp. 581-587.
Debets, Marjoke F. et al., "Aza-dibenzocyclooctynes for fast and efficient enzyme PEGylation via copper-free (3+2) cycloaddition", Chem Comm., vol. 46, 2010, pp. 97-99.
Einav, Shirit et al. "Prenylation inhibitors: a novel class of antiviral agets", J. Antimicrobial Chemotherapy, vol. 52, Issue 6, 2003, pp. 883-886.
El Kouni, Mahmoud H., "Trends in the Design of Nucleoside Analogues as Anti-HIV Drugs", Curr Pharm Des (2002), vol. 8, No. 8, pp. 581-593.
El Safadi, Y. et al., "HIV-1 reverse transriptase inhibitors", Applied Microbiology and Biotechnology, 75(4), 2007, pp. 721-737.
Emmelkamp et al., "CCR5 Antagonists: comparison of efficacy, side effects, pharmacokinetics and interactions—review of the literature", EurJ Med Res, vol. 12, 2007, pp. 409-417.
Engstova, Nana et al., "Natural and Azido Fatty Acids Inhibit Phosphate Transport and Activate Fatty Acid Anion Uniport Mediated by the Mitochondrial Phosphate Carrier", J. Biol. Chem., vol. 276, No. 7, 2001, pp. 4683-4691.

Erickson, J. et al., "Design, activity, and 2.8 A crystal structure of a C2 symmetric inhibitor complexed to HIV-1 protease", Science, 249, 1990, pp. 527-533.
Fenouillet, Emmanuel et al., "Effect of a glucosidase inhibitor on the bioativity and immunoreaclivity of human immunodeficiency virus type 1 envelope glycoprotein", J. Gen. Virol., vol. 72, 1991, pp. 1919-1926.
Freed, Eric, "Viral Late Domains", Journal of Virology, 76(10), 2002, pp. 4679-4687.
Geijtenbeek, T. F. et al., "a novel HiV reciptor on DCs that mediates HIV-1 transmission", Curr Top Microbial Immunol, vol. 276, 2003, pp. 31-54.
Gould, Stephen et al. "The trojan exosome Hypotheis", PNAS, 100 (19), 2003, pp. 10592-10597.
Graham et al. "Two-dimensional gel-based approaches for the assessment of N-linked and O-GlcNAc glycosylation in human and simian immunodeficiency viruses", Proteomics, vol. 8, No. 23-24, 2008, pp. 4919-4930.
Graham, David et al. "Cholesterol Depletion of Human Immunodeficiency Virus Type 1 and Simian Immunodeficiency Virus with B-Cyclodextrin Inactivates and Permeabilizes the Virions: Evidence for Virion-Associated Lipid Rafts", Journal of Virology, 77(5), 2003, pp. 8237-8248.
Guyader, Mirelle et al., "Role for Human Imminodeficiency Virus Type 1 Membrane Cholesterol in Viral Internatization", Journal of Virology, 76 (20), 2002, pp. 10356-10364.
Hang, Howard et al. "Chemical Probes for the Rapid Detection of Fatty-Acylated Proteins in Mammalian Cells", J. Am. Chem. Soc. 129 (10), 2007, pp. 2744-2745.
Hannoush, Rami et al, "Imaging the Lipidome: -Alkynyl fatty acids for Detection and Cellular Visualization of Lipid-Modified Proteins", ACS Chemical Biology, ACS Publications, 2009, pp. 1-20.
Henckel, Jennifer et al. "Influenza Virus M2 Protein Slows Traffic along the Secretory Pathway", J. Biol. Chem., vol. 273, Issue 11, 1998, pp. 6518-6524.
Herbeuval, Jean-Philippe et al., "HIV-1 Imminopathogenesis: How Good Interfeon Turns Bad", Clin. Immunol. 123 (2), 2007, pp. 121-128.
Hermida-Matsumoto, Luz et al., "Localization of Human Immunodeficiency Virus Type 1 Gag and Env at the Plasma Membrane by Confocal Imaging", Journal of Virology, 74 (18), 2000, pp. 8670-8679.
Johnson, Dr. et al., "Functional Analysis pf Protein N-Myristoylation: Metabolic Labeling Studies Using three Oxygen-Substituted Analogs of Myristic Acid and Cultured Mammalian Cells Provide Evidence for Protein-Sequence-Specific Incorporation and Alaong-Specific Redistribution", Proc. Natl. Acad. Sci. USA, 87, 1990 pp. 8511-8515.
Jordan, Stephen et al., "T Cell Glycolipid-Enriched Membrane Domains are Constitutively Assembled as Membrane Patches that Translocate to Immune Synapses", The Journal of Immunology, 171, 2003, pp. 78-87.
Kabouridis, P.S. et al., "Cholesterol depletion disrupts lipid rafts and modulates the activity of multiple signaling pathways in T lymphocytes", Eur J Immunol, vol. 30, 2000, pp. 954-963.
Kellam, Paul et al. "Fifth mutation in human immunodeficiency virus type 1 reverse transcriptase contributes to the development of high-level resistance to zidovudine", Medical Sciences, vol. 89, 1992, pp. 1934-1938.
Klei, Herbert E. et al., "X-Ray Crystal Structures of Human Immunodeficiency Virus Type 1 Protease Mutants Complexed with Atazanavir", Journal of Virology vol. 81, No. 17, 2007, pp. 9525-9535.
Kolb, H.C. et al., "Click Chemistry: Diverse Chemical Function from a Few Good Reactions", Angewandte Chemie International Edition in English, 40, 2001, pp. 2004-2021.
Kolchinsky, Peter et al., "Loss of a Single N-Linked Glycan Allows CD4-Independent Human Immunodeficiency Virus Type 1 Infecton by Altering the Position of the gp 120V1/V2 Variable Loops", Journal of Virology, 75 (7), 2001, pp. 3435-3443.
Kuritzkes, Daniel R. et al., "Antiretroviral activity of the anti-CD4 monoclonal antibody TNX-355 in patients infected with type 1", J. Infect Dis., vol. 189, 2004, pp. 286-291.

(56) References Cited

OTHER PUBLICATIONS

Kwong, P.D. et al., "HIV-1 evades antibody-mediated neutralization through conformational masking of receptor- binding sites", Nature, vol. 420, 2002, pp. 678-682.
La Bonte, Jason et al., "Enfuvirtide", Nature Reviews Drug Discovery, vol. 2, 2003, pp. 345-356.
Laast, V.A. et al., "Pathogenesis of simian immunodeficiency virus-induced alterations in macaque trigeminal ganglia", J Neuropathol Exp Neural, vol. 66, 2007, pp. 26-34.
Land, Aafke et al., "Folding of the Human Immunodeficiency Virus Type 1 Envelope Glycoprotein in the Endoplasmic reticulum", Biochimie 83, 2001, pp. 783-790.
Larder, Brendan A. et al., "HIV with Reduced Sensitivity to Zidovudine (AZT) Isolated During Prolonged Therapy", Science,1989, 243, pp. 1731-1734.
Lasky, Laurence A. et al., "Selectin-Carbohydrate Interactions and the Initiation of the Inflammatory Response", Annual Review Biochemistry, vol. 64, 1995, pp. 113-139.
Lewis, W.G. et al. "Click chemistry in Situ: Acetylcholinesterase as a Reaction Vessel for the Selectivity Asembly of a Femtomolar Inhibitor from an Array of building Blocks", Angewandte Chemie International Edition in English, 41 (6), 2002, p. 1053.
Liao, Z. et al. "Lipid Rafts and HIV Pathogenesis: Virion-Associated Cholesterol Is Required for Fusion and Infection of Susceptible Cells", AIDS Res Hum Retroviruses, vol. 19, 2003, pp. 675-687.
Lindwasser, O.W. et al., "Multimerization of Human Immunodeficiency Virus Type 1 Gag Promotes its Localization to Barges, Raft-Like Membrane Microdomains", Journal of Virology, 75 (17), 2001, pp. 7913-7924.
Magee, Anthony I. et al., "Are prenyl groups on proteins sticky fingers or greasy handles?", Biochem. J., vol. 376, 2003, pp. e3-e4.
Martin, Brent R. et al., "Large-Scale Prolifing of Protein Palmitoylation in Mammalian Cells", Nature Methods, Jan. 23, 2009, pp. 1-4.
Maury, Wendy et al., "Identification of Light-Independent Inhibition of Human Immunodeficiency Virus-1 Infection Through Bioguided Fractionation of Hypericum Perforatum", Virology Journal, 6 (101), 2009 pp. 1-12.
McTaggart, "Isoprenylated proteins", Cell. Mol. Life Sci., vol. 63, 2006, pp. 255-267.
Mitsuya, H. et al., "Molecular targets for AIDS therapy", Science, 249, 1990, pp. 1533-1544.
Mitsuya, H. et al., "Targeted Therapy of Human Immunodeficiency Virus-Related Disease", The FASEB Journal, 5(10), 1991, pp. 2369-2381.
Moore, John et al., "The Entry of Entry Inhibitors: A Fusion of Science and Medicine", PNAS, 100 (19), 2003, pp. 10598-10602.
Nguyen, Dzung et al., "Evidence for Budding of Human Immunodeficiency Virus Type 1 Selectively from Glycolipid-Enriched Membrane Lipid Rafts", Journal of Virology, 74(7), 2000, pp. 3264-3272.
Olson, Eric N. et al., "Fatty acylation of cellular proteins. Temporal and subcellular differences betwen palmitate and myristate acylation", J. Biol. Chem., vol. 261, No. 5, 1986, pp. 2458-2466.
Ono, Akira et al., "Plasma Membrane Rafts Play a Critical Role in HIV-1 Assembly and Release", PNAS, 98(24), 2001, pp. 13925-13930.
Palmer et al., "Tenofovir, adevovir, and zidovudine susceptibilities of primary human immunodeficiency virus type 1 isolates with non-B subtyps or nucleoside resistance", AIDS Res. Hum. Retroviruses, vol. 17, No. 12, 2001, pp. 1167-1173.
Parang, Keykavous et al., "Antiviral Activities of Myristic Acid Analogs Against Human Immunodeficiency and Hepatitis B Viruses", Antiviral Research, Elsevier BV, NL, vol. 34, No. 3:XP008072204, ISSN: 0166-3542, DOI: 10.1016/S0166-3542(96)01022-4, Jan. 1, 1997, pp. 75-90.
Paskaleva, Elena, "Palmitic Acid Analogs Exhibit Nanomolar Binding Affinity for the HIV-1 CD4 Receptor and Vanomolar Inhibition of gp120-to-CD4 Fusion", PLoS One 5(8), 2010, pp. 1-6.

Pike, Linda, "Rafts Defined: A Report on the Keystone Symposium on Lipid Rafts and Cell Function", Journal of Lipid Research, 47, 2006, pp. 1597-1598.
Resh, J. D., "The ubiquitous nature of budding", Trends Microbiol., vol. 9, 2001, pp. 57.
Rousso, Itay et al., "Palmitoylation of the HIV-1 Envelope Glycoprotein is critical for Viral Infectivity", PNAS, 97(25), 2000, pp. 13523-13525.
Rudd, Pauline M. et al., "Glcosylation and the Immune System", Science, vol. 291, Mar. 23, 2001, pp. 2370-2376.
Sakurai, Nagisa, "Detection of co-posttranslational protein N-myristoylation by metabolic labeling in an insect cell-free protein synthesis system", Analytical Biochemistry 362, 2007, pp. 236-244.
Sharma et al., "Nucleoside Inhibitors of Human Immunodeficiency Virus Type 1 Reverse Transcriptase", Cur. Top Med. Chem., (2004), vol. 4, No. 9, pp. 895-919.
Shi, Yu et al., "Evolution of Human Immunodeficincy Virus Type 1 Coreceptor Usage, Autologous Neutralization, Envelope Sequence and Glycosylation", Journal of General Virology, 86, 2005, pp. 3385-3396.
Smith, Douglas H. et al., "Blocking of HIV-1 infectivity by a soluble, secreted form of the CD4 antigen", Science, vol. 238, No. 4834,1987, pp. 1704-1707.
Stoffel, Wilhelm et al., "Lipids with photosensitive groups as chemical probes for the structural analysis of biological membranes. On the localization of the G- and M-protein of vesicular stomatitis virus", Hoppe-Seyler's Zeitschrift Fuer Physiologische Chemie, Walter De Gruyter, Berlin, DE, vol. 359, No. 8; XP009152164; ISSN: 0018-4888, Aug. 1, 1978, pp. 923-931.
Towler, Dwight et al., "Protein fatty acid acylation: enzymatic synthesis of an N-myristoylglycy peptide", Proc. Natl. Acad. Sci. USA, vol. 83, pp. 2812-2816.
Varki, Biological roles of oliosaccharides: All of the theories are correct, Glycobiology, vol. 3, No. 2, 1993, pp. 97-130.
Veazey, Ronald S. et al., "Protection of macaques from vaginal SHIV challenge by vaginally delivered inhibitors of virus-cell fusion", Nature, vol. 438, 2005, pp. 99-102.
Viard, Mathias et al., "Role of Cholesterol in Human Immunodeficiency Virus Type 1 Envelope Protein-Mediated Fusion with Host Cells", Journal of Virology, 76(22), 2002, pp. 11584-11595.
Viola, A. et al., "T-cell activation and the dynamic world of rafts", Apmis, vol. 107, 1997, pp. 615-623.
Viola, Antonella et al., "T Lymphocyte Costimulation Mediated by Reorganization of Membrane Microdomains", Science, 283, 1999, pp. 680-682.
Wells, Lance et al., "Glycosylation of Nucleocyptoplasmic Proteins: Signal Transduction and O-GicNAc", Science, vol. 291, Mar. 23, 2001, pp. 2376-2378.
Yang, Chinglai et al., "The Human and Simian Immunodeficiency Virus Envelope Glycoprotein Transmembrane Subunits are Palmitoylated", Proc. Natl. Acad. Sci. USA, 92, 1995, pp. 9871-9875.
Zachara, Natasha E. et al., "The Emergining Significance of O-GlcNAc in Cellular Regulation", Chemical Reviews, vol. 102, 2002, pp. 431-438.
Second Chinese Office Action dated Mar. 4, 2015, Chinese Application No. 201180046841.0 filed Jul. 28, 2011, pp. 1-3.
Shan, Woan-Eng et al., "Wild-Type-Like Replication Potential of Human Immunodeficiency Virus Type 1 Envelope Mutants Lacking Palmitoylation Signals", Journal of Virology, Jul. 2005, vol. 79, No. 13, pp. 8374-8387.
Devadas, Balekudru et al., "Substrate Specificity of Saccharomyces cerevisiae Myristoyl-CoA: Protein N-Myristoyltransferase", The Journal of Biological Chemistry, Apr. 15, 1992, vol. 287, No. 11, pp. 7224-7239.
Harper, David R and Gilbert, Ruth L, "Viral Lipoproteins", Rev. Med. Virol (1992), 2, pp. 107-115.
Bryant, Martin L. et al., "Myristylcoa: protein n-myristoyltransferase as a therapeutic target for inhibiting replication of human immunodeficiency virus-1", Perspectives in Drug Discovery and Design (1993), 1, pp. 193-209.

(56) References Cited

OTHER PUBLICATIONS

Rousso, Ray et al., "Palmitoylation of the hiv-1 envelope glycoprotein is critical for viral infectivity", PNAS (2000), 97(25), pp. 135213-13535.

Piroux, Nathalie et al., "Geminivirus pathogenicity protein C4 interacts with arabidopsis thaliana shaggy-rleated protein kinase Atsk eta, a component of the brassinosteroid signalling pathway" Virology (2007), 362, pp. 428-440.

Sasaki, Jun and Nakashima, Nobuhiko, "Translation initiation at the CUU codon is mediated by the internal ribosome entry site of an insect picorna-like virus in vitro", J. Virol. (1999), pp. 1219-1226.

Doms, Robert W. And More, John P., "HIV-1 membrane fusion: Targets of opportunity", J. Cell Bio. (2000), 151(2), pp. F9-F13.

European Patent Office Communication dated Jul. 3, 2015, European Patent Application No. 11 746 0675 filed Jun. 5, 2013, pp. 1-6.

Prescher et al., "Chemistry in linving systems", Nature Chemical Biology, Jun. 2005, vol. 1, No. 1, pp. 13-21.

The webage for solvent CAS 109-99-9 from Louisiana State University, http://macro.lsu.edu/HotTo/solvents/THF.htm, downloaded Oct. 17, 2017, 2 pages.

21 CFR 182.60, Code of Federal Regulations, Title 21, vol. 3, Revised as Apr. 1, 2016, 3 pages.

Abcam monograph on cell culture, https://web.archive.org/web/20100401013614, http://www.abcom/ps/pdf/protocols/cell_culture.pdf, downlaoded Apr. 1, 2010, 4 pages.

\* cited by examiner

ANTI-VIRAL AZIDE CONTAINING COMPOUNDS

CROSS REFERENCE TO RELATED APPLICATIONS

This application is a divisional of U.S. application Ser. No. 14/831,220 (Allowed), filed 20 Aug. 2015, which is a divisional of U.S. application Ser. No. 13/192,959, filed 28 Jul. 2011, now U.S. Pat. No. 9,144,575, which claims the benefit of U.S. Provisional No. 61/368,565, filed 28 Jul. 2010. The contents of all of which are hereby incorporated by reference in their entirety.

BACKGROUND

Viral infections account for significant morbidity and mortality in humans and animals. In addition, viral infections also result in significant agricultural losses, with plant viruses causing an estimated $60 billion in lost crop yields throughout the world each year. Although significant resources have been dedicated to identifying compounds having anti-viral properties, viral infections continue to present a significant risk to human health and agriculture.

In addition, the usefulness of most existing anti-viral treatments is limited by the development of multidrug resistance, poor efficacy, and/or toxicity. In fact, many anti-viral treatments are highly toxic and can cause serious side effects, including heart damage, kidney failure and osteoporosis. Other challenges include creating a drug that is broadly applicable in combating many different types of viral infections, which can be particularly important in the treatment of immunocompromised individuals.

One virus in particular, the human immunodeficiency virus (HIV), remains a global pandemic despite the development of antiretroviral drugs targeting HIV. As of 2007, it was estimated that more than 33 million people were infected with HIV, and HIV associated diseases represent a major world health problem. HIV is a retrovirus that infects CD4+ cells of the immune system, destroying or impairing their function. As the infection progresses, the immune system becomes weaker, leaving the infected person more susceptible to opportunistic infections and tumors, such as Kaposi's sarcoma, cervical cancer, lymphoma, and neurological disorders. The most advanced stage of HIV infection is acquired immunodeficiency syndrome (AIDS). It can take 10-15 years for an HIV-infected person to develop AIDS. Certain antiretroviral drugs can delay the process even further.

Although much effort has been put forth into designing effective therapeutics against HIV, currently no curative anti-retroviral drugs against HIV exist. Several stages of the HIV life cycle have been evaluated as targets for the development of therapeutic agents (Mitsuya, H. et al., 1991, *FASEB J* 5:2369-2381). One area of focus has been the HIV reverse transcriptase enzyme. Reverse transcriptase copies the HIV, single stranded RNA genome into double-stranded viral DNA. The viral DNA is then integrated into the host's chromosomal DNA where the host's cellular processes, like transcription and translation, are used to produce viral proteins and ultimately new virus particles. Therefore, interfering with reverse transcriptase inhibits HIV's ability to replicate. One class of reverse transcriptase inhibitors is nucleoside analogs, such as Zidovudine (AZT), Didanosine (ddI), Zalcitabine (ddC), and Stavudine (d4T), Lamivudine (3TC), Abacavir (ABC), Emtricitabine (FTC), Entecavir (INN), and Apricitabine (ATC) (Mitsuya, H. et al., 1991, *Science* 249:1533-1544; El Kouni, *Curr Pharm Des*, 2002, 8:581-93; Sharma et al., *Cur Top Med Chem*, 2004, 4:895-919). Another class of reverse transcriptase inhibitors is nucleotide analogs, such as Tenofovir (tenofovir disoproxil fumarate) and Adefovir (bis-POM PMPA) (Palmer et al., *AIDS Res Hum Retroviruses*, 2001, 17:1167-73). These nucleoside and nucleotide compounds are analogs of the naturally occurring deoxyribose nucleotides, however, the analogs lack the 3'-hydroxyl group on the deoxyribose sugar. As a result, when the analogs are incorporated into a growing viral DNA chain, the incoming deoxynucleotide cannot form a phosphodiester bond with the analog that is needed to extend the DNA chain. Thus, the analogs terminate viral DNA replication. Another class of reverse transcriptase inhibitors is the non-nucleoside reverse transcriptase inhibitors, such as Efavirenz, Nevirapine, Delavirdine, and Etravirine (El Safadi et al., *Appl Microbiol Biotechnol*, 2007, 75:723-37). They have a different mode of action than the nucleoside and nucleotide inhibitors, binding to the reverse transcriptase and interfering with its function.

The late stages of HIV replication involve processing of certain viral proteins prior to the final assembly of new virions. This late-stage processing is dependent, in part, on the activity of a viral protease. Thus, another area of focus in the development of antiretroviral drugs is protease inhibitors, such as saquinavir, ritonavir, indinavir, nelfinavir, amprenavir, lopinavir, and atazanavir (Erickson, J., 1990, *Science* 249:527-533; Klei et al., *J Virol*, 81:9525-35).

Other antiretroviral drugs target viral entry into the cell, the earliest stage of HIV infection. For HIV to enter a cell, its surface gp120 protein binds to CD4, exposing a conserved region of gp120 that binds to a CCR5 or a CXCR4 co-receptor. After gp120 binds to the co-receptor, a hydrophobic fusion peptide at the N-terminus of the gp41 envelope protein is exposed and inserted into the membrane of the cell. Entry inhibitors work by interfering with any stage of the viral entry process. For example, recombinant soluble CD4, for example, has been shown to inhibit infection of CD-4+ T-cells by some HIV-1 strains (Smith, D. H. et al., 1987, *Science* 238:1704-1707). Similarly, TNX-355 is a monoclonal antibody that binds CD4 and inhibits binding to gp120 (Kuritzkes et al., *J Infect Dis*, 2004, 189:286-91). BMS-806 binds to the viral envelope protein and inhibits binding to CD4 (Veazy et al., *Nature* 2003, 438:99-102). Co-receptor binding can be inhibited by several CCR5 inhibitors, including SCH-C and SCH-D, UK-427,857, maraviroc, vicriviroc, and an anti-CCR5 antibody (PRO-140) (Emmelkamp et al., *Eur J Med Res*, 2007, 12:409-17). Co-receptor binding can also be inhibited by the CXCR4 inhibitors AMD3100 and AMD070 (De Clerq, *Nature Reviews Drug Discovery* 2003, 2:581-87). Other compounds, such as enfuvirtide, bind to gp41 and interfere with its ability to mediate membrane fusion and entry (La Bonte et al., *Nature Reviews Drug Discovery* 2003, 2:345-36).

While beneficial, these antiretroviral drugs often exhibit toxic side effects such as bone marrow suppression, vomiting, and liver function abnormalities. In addition, they are not curative, probably due to the rapid appearance of drug resistant HIV mutants (Lander, B. et al., 1989, Science 243:1731-1734). Drug-resistant HIV strains develop due to the very high genetic variability of HIV. This genetic variability results from several factors, including HIV's fast replication cycle, with the generation of $10^9$ to $10^{10}$ virions per day, a high mutation rate of approximately $3 \times 10^{-5}$ per nucleotide base per cycle of replication, and recombinogenic properties of reverse transcriptase.

To combat the development of drug resistant HIV strains, multiple drugs have been combined as part of highly active antiretroviral therapy (HAART) (El Safadi et al., *Appl Microbiol Biotechnol*, 2007, 75:723-37; Sharma et al., *Cur Top Med Chem*, 2004, 4:895-919). Currently HAART typically involves combining at least three drugs belonging to at least two classes of antiretroviral agents. As discussed above, these classes include nucleoside or nucleotide analog reverse transcriptase inhibitors, non-nucleoside reverse transcriptase inhibitors, protease inhibitors, and entry inhibitors.

Thus, although a great deal of effort is being directed to the design and testing of anti-viral drugs, the search for new and improved methods of treating viral infections, such as HIV, continues.

SUMMARY

The present disclosure provides methods of using azide-modified biomolecules, such as azide-modified fatty acids, azide-modified carbohydrates, azide-modified isoprenoid lipids, or pharmaceutically acceptable salt thereof, for treating viral infections, such as HIV infections, or for labeling a protein of a virus, such as HIV, as well as pharmaceutical compositions containing an azide-modified biomolecule or pharmaceutically acceptable salt thereof.

One aspect of the disclosure is directed to a method of treating a subject infected with a plant, an insect, or an animal virus and in need of treatment for the infection, the method comprising administering to the subject a therapeutically effective amount of an azide-modified fatty acid, an azide-modified carbohydrate, an azide-modified isoprenoid lipid or pharmaceutically acceptable salt thereof.

In some embodiments, the the azide-modified fatty acid or pharmaceutically acceptable salt thereof has the formula:

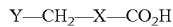

Y—CH$_2$—X—CO$_2$H  [I]

wherein,

Y is H or an azido group; and when Y is an azido group, X is a linear or branched carbon chain comprising 6 to 28 carbons, wherein one or more of said carbons may be independently replaced by an oxygen, selenium, silicon, sulfur, SO, SO$_2$ or NR$_1$, or wherein one or more pairs of said carbons adjacent to one another may be attached to one another by a double or triple bond; or when Y is H, X is a linear or branched carbon chain comprising 6 to 28 carbons, wherein one hydrogen on one of said carbons is replaced with an azido group and wherein one or more of said carbons not having an the azido group attached thereto may be independently replaced by an oxygen, selenium, silicon, sulfur, SO, SO$_2$ or NR$_1$, or wherein one or more pairs of said carbons adjacent to one another and not having an azido group may be attached to one another by a double or triple bond;

wherein, R$_1$ is H or an alkyl comprising 1 to 6 carbons.

In some of these embodiments, Y is an azido group. In some of these, X is a linear carbon chain. In some of these, the linear carbon chain comprises 8 to 15 carbons. In some of these, the linear carbon chain does not contain an oxygen, selenium, silicon, sulfur, SO, SO$_2$ or NR$_1$. In some of these, the carbon chain does not contain a double or triple bond. In some of these, the azide modified fatty acid is 15-azidopentadecanoic acid, 12-azidododecanoic acid, or pharmaceutically acceptable salt thereof.

In some embodiments, the azide-modified carbohydrate is an N-linked carbohydrate or an O-linked carbohydrate. In some embodiments, the azide-modified carbohydrate is tetraacetylated N-azidoacetylgalactosamine, tetraacetylated N-azidoacetyl-D-mannosamine, or tetraacetylated N-azidoacetylglucosamine.

In some embodiments, the azide-modified isoprenoid lipid comprises a farnesyl group or a geranylgeranyl group. In some of these, the azide-modified isoprenoid lipid is an azido farnesyl diphosphate, an azido farnesyl alcohol, an azido geranylgeranyl diphosphate, or an azido geranylgeranyl alcohol.

In some embodiments, the virus is an non-human animal virus or a human animal virus.

In some embodiments, the non-human animal virus is a picornavirus, a pestivirus, an arterivirus, a coronavirus, a paramyxovirus, an orthomyxovirus, a reovirus, a porcine, a circovirus, a herpesvirus, an asfarvirus, a retrovirus, a flavivirus, or a rhabdovirus.

In some of embodiments, the human animal virus is an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus. In some of these, the retrovirus is a human immunodeficiency virus or a human T-lymphotrophic virus. In some of these, the retrovirus is the human immunodeficiency virus, HIV-1.

In some embodiments, the virus is a plant virus. In some of these, the plant virus is an alfamovirus, an allexivirus, an alphacryptovirus, an anulavirus, an apscaviroid, an aureusvirus, an avenavirus, an aysunviroid, a badnavirus, a begomovirus, a benyvirus, a betacryptovirus, a betaflexiviridae, a bromovirus, a bymovirus, a capillovirus, a carlavirus, a carmovirus, a caulimovirus, a cavemovirus, a cheravirus, a closterovirus, a cocadviroid, a coleviroid, a comovirus, a crinivirus, a cucumovirus, a curtovirus, a cytorhabdovirus, a dianthovirus, an enamovirus, an umbravirus & B-type satellite virus, a fabavirus, a fijivirus, a furovirus, a hordeivirus, a hostuviroid, an idaeovirus, an ilarvirus, an ipomovirus, a luteovirus, a machlomovirus, a macluravirus, a marafivirus, a mastrevirus, a nanovirus, a necrovirus, a nepovirus, a nucleorhabdovirus, an oleavirus, an ophiovirus, an oryzavirus, a panicovirus, a pecluvirus, a petuvirus, a phytoreovirus, a polerovirus, a pomovirus, a pospiviroid, a potexvirus, a potyvirus, a reovirus, a rhabdovirus, a rymovirus, a sadwavirus, a SbCMV-like virus, a sequivirus, a sobemovirus, a tenuivirus, a TNsatV-like satellite virus, a tobamovirus, a topocuvirus, a tospovirus, a trichovirus, a tritimovirus, a tungrovirus, a tymovirus, an umbravirus, a varicosavirus, a vitivirus, or a waikavirus.

In some embodiments, the virus is an insect virus. In some of these, the insect virus is a densovirus, an iridovirus, a chloriridovirus, a baculovirus, a polydnavirus, an entomopox virus, an ascovirus, an insect picornavirus, a calicivirus, or a nodavirus.

In some embodiments, the subject is a human animal.

Another aspect of the disclosure is directed a method of inhibiting the infectivity of a virus, the method comprising contacting a cell infected with the virus with an azide-modified fatty acid, an azide-modified carbohydrate, an azide-modified isoprenoid lipid, or pharmaceutically acceptable salt thereof in an amount effective to inhibit the infectivity of the virus.

In some embodiments, the azide-modified fatty acid or pharmaceutically acceptable salt thereof has the Formula [I], as described above. In some of these, Y is an azido group. In some of these, X is a linear carbon chain. In some of these, the linear carbon chain comprises 8 to 15 carbons. In some of these, the linear carbon chain does not contain an oxygen, selenium, silicon, sulfur, SO, $SO_2$ or $NR_1$. In some of these, the carbon chain does not contain a double or triple bond. In some of these, the azide modified fatty acid is 15-azidopentadecanoic acid, 12-azidododecanoic acid, or pharmaceutically acceptable salt thereof.

In some embodiments, the azide-modified carbohydrate is an N-linked carbohydrate or an O-linked carbohydrate. In some embodiments, the azide-modified carbohydrate is tetraacetylated N-azidoacetylgalactosamine, tetraacetylated N-azidoacetyl-D-mannosamine, or tetraacetylated N-azidoacetylglucosamine.

In some embodiments, the azide-modified isoprenoid lipid comprises a farnesyl group or a geranylgeranyl group. In some of these, the azide-modified isoprenoid lipid is an azido farnesyl diphosphate, an azido farnesyl alcohol, an azido geranylgeranyl diphosphate, or an azido geranylgeranyl alcohol.

In some embodiments, the virus is a non-human animal virus or human animal virus.

In some embodiments, the virus is a non-human animal virus. In some embodiments, the non-human animal virus is a picornavirus, a pestivirus, an arterivirus, a coronavirus, a paramyxovirus, an orthomyxovirus, a reovirus, a porcine, a circovirus, a herpesvirus, an asfarvirus, a retrovirus, a flavivirus, or a rhabdovirus.

In some of embodiments, the virus is a human animal virus. In some of these, the human animal virus is an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus. In some of these, the retrovirus is a human immunodeficiency virus or a human T-lymphotrophic virus. In some of these, the retrovirus is the human immunodeficiency virus, HIV-1.

In some embodiments, the virus is a plant virus. In some of these, the plant virus is an alfamovirus, an allexivirus, an alphacryptovirus, an anulavirus, an apscaviroid, an aureusvirus, an avenavirus, an aysunviroid, a badnavirus, a begomovirus, a benyvirus, a betacryptovirus, a betaflexiviridae, a bromovirus, a bymovirus, a capillovirus, a carlavirus, a carmovirus, a caulimovirus, a cavemovirus, a cheravirus, a closterovirus, a cocadviroid, a coleviroid, a comovirus, a crinivirus, a cucumovirus, a curtovirus, a cytorhabdovirus, a dianthovirus, an enamovirus, an umbravirus & B-type satellite virus, a fabavirus, a fijivirus, a furovirus, a hordeivirus, a hostuviroid, an idaeovirus, an ilarvirus, an ipomovirus, a luteovirus, a machlomovirus, a macluravirus, a marafivirus, a mastrevirus, a nanovirus, a necrovirus, a nepovirus, a nucleorhabdovirus, an oleavirus, an ophiovirus, an oryzavirus, a panicovirus, a pecluvirus, a petuvirus, a phytoreovirus, a polerovirus, a pomovirus, a pospiviroid, a potexvirus, a potyvirus, a reovirus, a rhabdovirus, a rymovirus, a sadwavirus, a SbCMV-like virus, a sequivirus, a sobemovirus, a tenuivirus, a TNsatV-like satellite virus, a tobamovirus, a topocuvirus, a tospovirus, a trichovirus, a tritimovirus, a tungrovirus, a tymovirus, an umbravirus, a varicosavirus, a vitivirus, or a waikavirus.

In some embodiments, the virus is an insect virus. In some of these, the insect virus is a densovirus, an iridovirus, a chloriridovirus, a baculovirus, a polydnavirus, an entomopox virus, an ascovirus, an insect picornavirus, a calicivirus, or a nodavirus.

In some embodiments, the cell is a human cell.

A third aspect of the disclosure is directed to a method of producing a virus labeled with an azide-modified fatty acid, an azide-modified carbohydrate, an azide-modified isoprenoid lipid, or pharmaceutically acceptable salt thereof, the method comprising contacting a cell infected with the virus with the azide-modified fatty acid, the azide-modified carbohydrate, the azide-modified isoprenoid lipid, or pharmaceutically acceptable salt thereof so that the azide-modified fatty acid, the azide-modified carbohydrate, or the azide-modified isoprenoid lipid enters the cell and is incorporated into a protein of the virus, thereby producing the labeled virus.

In some embodiments, the method is a method of producing a human immunodeficiency virus labeled with an azide-modified fatty acid, an azide-modified carbohydrate, an azide-modified isoprenoid lipid, or pharmaceutically acceptable salt thereof, the method comprising contacting a cell infected with the human immunodeficiency virus with the azide-modified fatty acid, the azide-modified carbohydrate, the azide-modified isoprenoid lipid, or pharmaceutically acceptable salt thereof so that the azide-modified fatty acid, the azide-modified carbohydrate, the azide-modified isoprenoid lipid, or pharmaceutically acceptable salt thereof enters the cell and is incorporated into a protein of the virus, thereby producing the labeled virus.

In some embodiments, the azide-modified fatty acid or pharmaceutically acceptable salt thereof has the Formula [I], as described above. In some of these, Y is an azido group. In some of these, X is a linear carbon chain. In some of these, the linear carbon chain comprises 8 to 15 carbons. In some of these, the linear carbon chain does not contain an oxygen, selenium, silicon, sulfur, SO, $SO_2$ or $NR_1$. In some of these, the carbon chain does not contain a double or triple bond. In some of these, the azide modified fatty acid is 15-azidopentadecanoic acid, 12-azidododecanoic acid, or pharmaceutically acceptable salt thereof.

In some embodiments, the azide-modified carbohydrate is an N-linked carbohydrate or an O-linked carbohydrate. In some embodiments, the azide-modified carbohydrate is tetraacetylated N-azidoacetylgalactosamine, tetraacetylated N-azidoacetyl-D-mannosamine, or tetraacetylated N-azidoacetylglucosamine.

In some embodiments, the azide-modified isoprenoid lipid comprises a farnesyl group or a geranylgeranyl group. In some of these, the azide-modified isoprenoid lipid is an azido farnesyl diphosphate, an azido farnesyl alcohol, an azido geranylgeranyl diphosphate, or an azido geranylgeranyl alcohol.

In some embodiments, the cell is a human cell.

In some embodiments, the virus is a human immunodeficiency virus, while in others, the virus is a baculovirus.

In some embodiments, the azide-modified carbohydrate, azide-modified fatty acid, azide-modified isoprenoid lipid, or pharmaceutically acceptable salt thereof is formulated with a pharmaceutically acceptable excipient.

In some embodiments, the method further comprises the step of administering to the subject the the azide-modified carbohydrate, azide-modified fatty acid, azide-modified isoprenoid lipid, or pharmaceutically acceptable salt thereof which is formulated with a pharmaceutically acceptable excipient.

A fourth aspect of the disclosure is directed to a method of tracking a virus in vivo comprising the steps of contacting cultured cells or a subject with an azide-modified carbohydrate, azide-modified fatty acid, azide-modified isoprenoid lipid, or a pharmaceutically acceptable salt thereof; contacting the cultured cells or the subject with an alkyne labeled reporter molecule; and tracking the reporter-labeled virus in the cultured cells or the subject.

In some embodiments, the cultured cells or the subject is contacted with an azide-modified fatty acid or pharmaceutically acceptable salt thereof.

In some embodiments, the azide-modified fatty acid or pharmaceutically acceptable salt thereof has the Formula [I], as described above. In some embodiments, Y is an azido group. In some of these, X is a linear carbon chain. In some of these, the linear carbon chain comprises 8 to 15 carbons. In some of these, the linear carbon chain does not contain an oxygen, selenium, silicon, sulfur, SO, $SO_2$ or $NR_1$. In some of these, the carbon chain does not contain a double or triple bond. In some of these, the azide modified fatty acid is 15-azidopentadecanoic acid, 12-azidododecanoic acid, or pharmaceutically acceptable salt thereof.

Yet another aspect of the disclosure is directed to a pharmaceutical composition comprising an azide-modified fatty acid, an azide-modified carbohydrate, an azide-modified isoprenoid lipid, or pharmaceutically acceptable salt thereof and a pharmaceutically acceptable excipient.

In some embodiments, the azide-modified fatty acid or pharmaceutically acceptable salt thereof has the Formula [I], as described above. In some of these, Y is an azido group. In some of these, X is a linear carbon chain. In some of these, the linear carbon chain comprises 8 to 15 carbons. In some of these, the linear carbon chain does not contain an oxygen, selenium, silicon, sulfur, SO, $SO_2$ or $NR_1$. In some of these, the carbon chain does not contain a double or triple bond. In some of these, the azide modified fatty acid is 15-azidopentadecanoic acid, 12-azidododecanoic acid, or pharmaceutically acceptable salt thereof.

In some embodiments, the azide-modified carbohydrate is an N-linked carbohydrate or an O-linked carbohydrate. In some embodiments, the azide-modified carbohydrate is tetraacetylated N-azidoacetylgalactosamine, tetraacetylated N-azidoacetyl-D-mannosamine, or tetraacetylated N-azidoacetylglucosamine.

In some embodiments, the azide-modified isoprenoid lipid comprises a farnesyl group or a geranylgeranyl group. In some of these, the azide-modified isoprenoid lipid is an azido farnesyl diphosphate, an azido farnesyl alcohol, an azido geranylgeranyl diphosphate, or an azido geranylgeranyl alcohol.

In some embodiments, the composition further comprises at least one anti-viral agent. In some of these, the anti-viral agent is selected from a reverse transcriptase inhibitor, a viral protease inhibitor, a viral fusion inhibitor, a viral integrase inhibitor, a glycosidase inhibitor, a viral neuraminidase inhibitor, an M2 protein inhibitor, an amphotericin B, hydroxyurea, α-interferon, β-interferon, γ-interferon, and an antisense oligonucleotide. In some of these, the reverse transcriptase inhibitor is at least one of Zidovudine (AZT), Didanosine (ddI), Zalcitabine (ddC), ddA, Stavudine (d4T), Lamivudine (3TC), Abacavir (ABC), Emtricitabine (FTC), Entecavir (INN), Apricitabine (ATC), Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine; wherein the virus protease inhibitor is at least one of tipranavir, darunavir, indinavir, lopinavir, fosamprenavir, atazanavir, saquinavir, ritonavir, indinavir, nelfinavir, or amprenavir; wherein the viral fusion inhibitor is at least one of a CD4 antagonist, a CCR5 antagonist, a CXCR4 antagonist, or enfuvirtide; wherein the viral integrase is raltegravir; wherein the glycosidase inhibitor is at least one of SC-48334 or MDL-28574; wherein the viral neuraminidase inhibitor is at least one of oseltamivir, peramivir, zanamivir, and laninamivir; and wherein the M2 protein inhibitor is at least one of amantadine or rimantidine.

In some embodiments, the composition further comprises an agent for delivering the azide-modified fatty acid, the azide-modified carbohydrate, the azide-modified isoprenoid lipid or pharmaceutically acceptable salt thereof to a cell. In some of these, an agent for delivering the azide-modified fatty acid, the azide-modified carbohydrate, or the azide-modified isoprenoid lipid to a cell.

BRIEF DESCRIPTION OF THE DRAWINGS

The accompanying drawings, which are incorporated in and constitute a part of this specification, illustrate certain embodiments of the invention, and together with the written description, serve to explain certain principles of the invention.

DEFINITIONS

Figure 1:
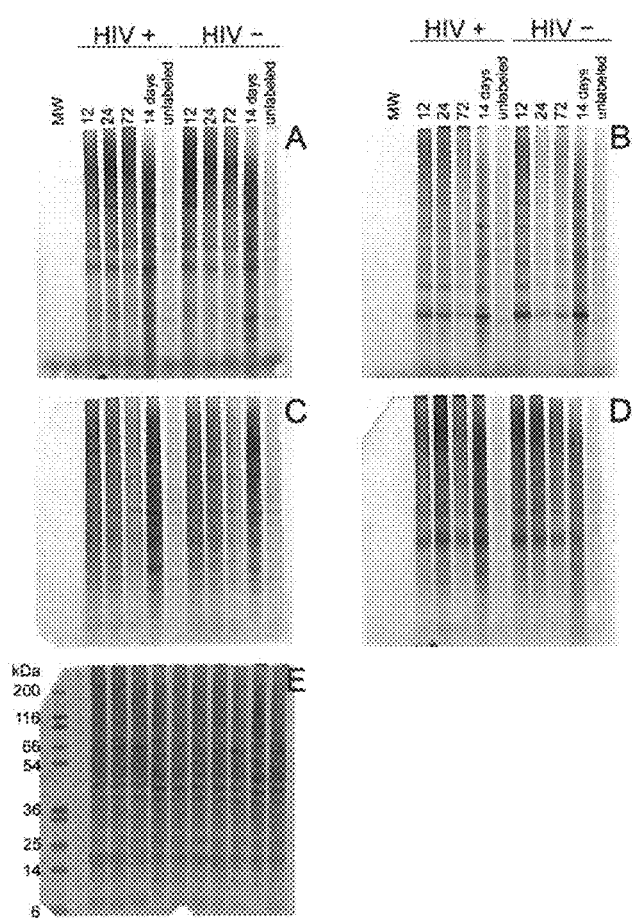
FIG. 1 shows a time course of azide-modified proteins in HIV-infected CEMx174 cells. CEMx174 infected cells were labeled with either (A) 15-azidopentadecanoic acid, (B) 12-azidododecanoic acid, (C) tetraacetylated N-azidoacetyl-galactosamine, or (D) tetraacetylated N-azidoacetyl-D-mannosamine and were harvested at 12, 24, 72 hours, and 14 days post-infection. Panel (E) shows a representative gel that was post-stained with the total protein stain: SYPRO® Ruby protein stain (Sigma-Aldrich, St. Louis, Mo.).

Unless defined otherwise, all technical and scientific terms used herein have the same meaning as commonly understood by one of ordinary skill in the art to which this invention is related. In order that the present invention may be more readily understood, certain terms are first defined. Additional definitions are set forth throughout the detailed description. In case of conflict, the present specification, including definitions, will control.

As used herein, "azide-modified fatty acid" refers to a fatty acid that comprises an azido group and has the following formula, R—$N_3$ where R comprises a hydrocarbon chain with at least one carboxylic acid functional group, which is usually, although not necessarily, at a terminal position.

As used herein, "azide-modified carbohydrate" refers to a carbohydrate that comprises an azido group and has the following formula, R—$N_3$ where R is a carbohydrate.

As used herein, "azide-modified isoprenoid lipid" refers to an isoprene-containing lipid, or derivative thereof. The azide-modified isoprenoid comprises an azido group and has the following formula, R—$N_3$ where R is an isoprene-containing lipid, such as the $C_{15}$ farnesyl isoprenoid lipid or the $C_{20}$ geranylgeranyl isoprenoid lipid, or a derivative thereof, including, but not limited to, an azido farnesyl diphosphate, an azido farnesyl alcohol, an azido geranylgeranyl diphosphate, or an azido geranylgeranyl alcohol.

As used herein, "animal virus" refers to a virus that infects a non-human animal or human animal cell. A non-human animal virus infects non-human animal cells. In certain instances, a virus that infects non-human animal cells is also capable of infecting human animal cells. A human animal virus infects human animal cells. In certain instances, a virus that infects human animal cells is also capable of infecting non-human animal cells.

As used herein, "biomolecule," refers to proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides, polysaccharides, which having characteristics typical of molecules found in living organisms and may be naturally occurring or may be artificial (not found in nature and not identical to a molecule found in nature).

As used herein, "click chemistry," refers to the copper(I)-catalyzed variant of the Huisgen cycloaddition or the 1,3-dipolar cycloaddition between an azide and a terminal alkyne to form a 1,2,4-triazole. Such chemical reactions can use, but are not limited to, simple heteroatomic organic reactants and are reliable, selective, stereospecific, and exothermic.

As used herein, "cycloaddition" refers to a chemical reaction in which two or more π (pi)-electron systems (e.g., unsaturated molecules or unsaturated parts of the same molecule) combine to form a cyclic product in which there is a net reduction of the bond multiplicity. In a cycloaddition, the π (pi) electrons are used to form new π (pi) bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Bertozzi et al. J. Am. Chem. Soc., 2004, 126:15046-15047.

As used herein, "DNA virus" refers to a virus that has deoxyribonucleic acid (DNA) as its genetic material. DNA viruses are usually double stranded but may also be single stranded.

As used herein, "glycoprotein" refers to a protein that has been glycosylated and those that have been enzymatically modified, in vivo or in vitro, to comprise a carbohydrate group.

As used herein, "HIV" and "human immunodeficiency virus" refer to human immunodeficiency virus 1 and 2 (HIV-1 and HIV-2).

As used herein, "infectivity" refers to the ability of a virus to enter or exit a cell.

As used herein, "insect virus" refers to a virus that infects insect cells. Certain insect viruses, such as, for example, unmodified baculovirus or modified baculovirus (BacMam), can also infect non-human animal and/or human animal cells.

As used herein, "plant virus" refers to a virus that infects plant cells.

As used herein, "pharmaceutically acceptable excipient" includes solvents, dispersion media, diluents, coatings, anti-bacterial and antifungal agents, isotonic and absorption delaying agents, etc., that are compatible with pharmaceutical administration. Use of these agents for pharmaceutically active substances is well known in the art.

As used herein, "protein" and "polypeptide" are used in a generic sense to include polymers of amino acid residues of any length. The term "peptide" is used herein to refer to polypeptides having less than 100 amino acid residues, typically less than 10 amino acid residues. The terms apply to amino acid polymers in which one or more amino acid residues are an artificial chemical analogue of a corresponding naturally occurring amino acid, as well as to naturally occurring amino acid polymers.

As used herein, "reporter molecule" refers to any moiety capable of being attached to a modified post translationally modified protein of the present invention, and detected either directly or indirectly. Reporter molecules include, without limitation, a chromophore, a fluorophore, a fluorescent protein, a phosphorescent dye, a tandem dye, a particle, a hapten, an enzyme and a radioisotope. Preferred reporter molecules include fluorophores, fluorescent proteins, haptens, and enzymes.

As used herein, "RNA virus" refers to a virus that has ribonucleic acid (RNA) as its genetic material. RNA viruses are usually single stranded but may also be double stranded.

As used herein, the term "subject" is intended to include human and non-human animals, plants, and insects. Subjects may include a human patient having a viral infection, including, but not limited to, an HIV infection. The term "non-human animals" of the invention includes all vertebrates, such as non-human primates, sheep, dogs, cats, cows, goats, horses, chickens, pigs, amphibians, reptiles, etc.

As used herein, "treatment" or "treating" refers to a therapeutic or preventative measure. The treatment may be administered to a subject having a disorder which may include, but is not limited to, a medical disorder in the case where the subject is an animal, or who ultimately may acquire the disorder, in order to prevent, cure, delay, reduce the severity of, and/or ameliorate one or more symptoms of a disorder or recurring disorder, or in order to prolong the survival of a subject beyond that expected in the absence of such treatment.

As used herein, a "therapeutically effective amount" or "effective amount" means the amount of a compound that, when administered to a non-human animal or human animal, a plant, an insect, or other subject for treating a disease, is sufficient to effect such treatment for the disease. The "effective amount" will vary depending on the compound, the disease and its severity and the age, weight, etc., of the subject to be treated.

It must be noted that, as used in this specification and the appended claims, the singular form "a", "an" and "the" include plural referents unless the context dictates otherwise. Thus, for example, reference to "a virus" includes a plurality of viruses unless the context dictates otherwise.

While this invention has been particularly shown and described with references to preferred embodiments thereof, it will be understood by those skilled in the art that various changes in form and details may be made therein without departing from the scope of the invention encompassed by the appended claims. In addition, the materials, methods, and examples are illustrative only and not intended to be limiting. All publications, patent applications, patents, and other references mentioned herein are incorporated by reference in their entirety.

DETAILED DESCRIPTION

The present disclosure concerns the use of azide-modified biomolecules, such as fatty acids or carbohydrates, for treating viral infections, as well as pharmaceutical compositions containing an azide-modified biomolecule. Azide-modified fatty acids, azide-modified carbohydrates, and azide-modified isoprenoid lipids have been previously described as useful reagents for labeling and detecting proteins of interest as part of a click chemistry reaction involving a copper (I)-catalyzed cycloaddition reaction between an azide and an alkyne. See CLICK-IT® metabolic labeling reagents for proteins (Invitrogen, Carlsbad, Calif.); see also, U.S. Patent Application Publication No. 2007/0249014 and U.S. Patent Application Publication No. 20050222427, which disclosures are hereby incorporated by reference in its entirety. Applicants, however, have unexpectedly discovered that these azide-modified biomolecules have anti-viral activity and can be used to treat viral infections. It was surprisingly discovered that these azide-modified biomolecules profoundly affect viral infectivity and that labeling viruses with these azide-modified biomolecules inhibited viral entry into host cells. Without intending to be bound by any theory, it appears that post-translational modification of viral proteins with an azido-modified biomolecule at sites normally occupied by unmodified biomolecules, such as saturated fatty acids (e.g., myristic acid and palmitic acid), may result in the inhibition of infectivity of the virus in a manner similar to the absence of these biomolecules at these sites.

Click Chemistry

Azides and terminal or internal alkynes can undergo a 1,3-dipolar cycloaddition (Huisgen cycloaddition) reaction to give a 1,2,3-triazole. However, this reaction requires long reaction times and elevated temperatures. Alternatively, azides and terminal alkynes can undergo Copper(I)-catalyzed Azide-Alkyne Cycloaddition (CuAAC) at room temperature. Such copper(I)-catalyzed azide-alkyne cycloadditions, also known as click chemistry, is a variant of the Huisgen 1,3-dipolar cycloaddition wherein organic azides and terminal alkynes react to give 1,4-regioisomers of 1,2,3-triazoles. Examples of click chemistry reactions are described by Sharpless et al. (U.S. Patent Application Publication No. 20050222427, PCT/US03/17311; Lewis W G, et al., Angewandte Chemie-Int'l Ed. 41 (6): 1053; method reviewed in Kolb, H. C., et al., Angew. Chem. Inst. Ed. 2001, 40:2004-2021), which developed reagents that react with each other in high yield and with few side reactions in a heteroatom linkage (as opposed to carbon-carbon bonds) in order to create libraries of chemical compounds.

Click chemistry has been used to label and detect proteins of interest. For example, the CLICK-IT® (Invitrogen, Carlsbad, Calif.) reaction is a two-step labeling technique involving the incorporation of a modified metabolic precursor, such as an azide-modified fatty acid, an azide-modified carbohydrate, or an azide-modified isoprenoid lipid, into proteins as a chemical "handle" followed by the chemoselective ligation (or "click" reaction) between an azide and an alkyne. In the click reaction, the modified protein is detected with a corresponding azide- or alkyne-containing dye or hapten. The CLICK-IT® metabolic labeling reagents have been used to monitor post translational modifications of proteins, such as acylation, glycosylation, and prenylation, and include 1) azide-modified fatty acids, such as CLICK-IT® palmitic acid azide (i.e., 15-azidopentadecanoic acid) and CLICK-IT® myristic acid azide (i.e., 12-azidododecanoic acid), for labeling palmitoylated and myristoylated proteins, respectively; 2) azide-modified carbohydrates, including CLICK-IT® GalNAz (tetraacetylated N-azidoacetylgalactosamine) for labeling O-linked glycoproteins, CLICK-IT® ManNAz (tetraacetylated N-azidoacetyl-D-mannosamine) for labeling sialic acid modified glycoproteins, and CLICK-IT® GlcNAz (tetraacetylated N-azidoacetylglucosamine) for labeling O-GlcNAz-modified glycoproteins; and 3) azide-modified isoprenoid lipids, such as CLICK-IT® farnesyl alcohol azide and CLICK-IT® geranylgeranyl alcohol azide. As noted above, Applicants, have unexpectedly found that these azide-modified biomolecules have anti-viral activity and can be used to treat viral infections.

Glycosylation

Glycosylation is an enzymatic process in which carbohydrates are attached to proteins, lipids, or other organic molecules in a cell. Glycoproteins are biomolecules composed of proteins covalently linked to carbohydrates. Certain post-translational modifications append a sugar moiety (carbohydrate) onto a protein, thereby forming a glycoprotein. The common monosaccharides found in glycoproteins include, but are not limited to, glucose, galactose, mannose, fucose, xylose, N-acetylgalactosamine (GalNAc), N-acetylglucosamine (GlcNAc) and N-acetylneuraminic acid (NANA, also known as sialic acid). N-acetyl-D-mannosamine (ManNAc) is a precursor of the neuraminic acids, including NANA. Two of the same or different monosaccharides can join together to form a disaccharide. The addition of more monosaccharides results in the formation of oligosaccharides of increasing length. In addition, the sugar moiety can be a glycosyl group.

In glycoproteins, the carbohydrates can be linked to the protein component by either N-glycosylation or O-glycosylation. N-glycosylation commonly occurs through a nitrogen on an asparagine or arginine side chain, forming an N-glycosidic linkage via an amide group. O-glycosylation commonly occurs at the hydroxy oxygen of hydroxylysine, hydroxyproline, serine, tyrosine or threonine side chains, forming an O-glycosidic linkage. GalNAc and GlcNAc are both O-linked carbohydrates. Sialic acid is found on both N- and O-linked carbohydrates.

Protein glycosylation is one of the most abundant post-translational modifications and plays a fundamental role in the control of biological systems. For example, glycosylation influences protein folding and can help to stabilize proteins and prevent their degradation. Glycosylation also can affect a protein's ability to bind to other molecules and mediate intra- or inter-cellular signaling pathways. For example, carbohydrate modifications are important for host-pathogen interactions, inflammation, development, and malignancy (Varki, A. *Glycobiology* 1993, 3, 97-130; Lasky, L. A. *Annu. Rev. Biochem.* 1995, 64, 113-139. (c) Capila, I.; Linhardt, R. J. *Angew. Chem., Int. Ed.* 2002, 41, 391-412; Rudd, P. M.; Elliott, T.; Cresswell, P.; Wilson, I. A.; Dwek, R. A. *Science* 2001, 291, 2370-2376). One such covalent modification is O-GlcNAc glycosylation, which is the covalent modification of serine and threonine residues by D-N-acetylglucosamine (Wells, L.; Vosseller, K.; Hart, G. W. *Science* 2001, 291, 2376-2378; Zachara, N. E.; Hart, G. W. *Chem. Rev.* 2002, 102, 431). The O-GlcNAc modification is found in all higher eukaryotic organisms from *C. elegans* to man and has been shown to be ubiquitous, inducible and highly dynamic, suggesting a regulatory role analogous to phosphorylation.

Fatty Acid Acylation

Fatty acid acylation is an enzymatic process in which fatty acids are attached to proteins in a cell. This process can affect a protein's function as well as its cellular location and is common to proteins of both cellular and viral origin (Towler et al., *Proc Natl Acad Sci USA* 1986, 83:2812-16). Myristic acid and palmitic acid are the two most common fatty acids that are attached to proteins (Olson et al., *J Biol Chem* 261(5):2458-66). Generally myristic acid is attached to soluble and membrane proteins via an amide linkage to an amino terminal glycine exposed during removal of an N-methionine residue, although it can also attach to other amino acids. Myristoylation can also occur post-translationally, for example, when a protease cleaves a polypeptide and exposes a glycine residue. Palmitic acid is attached to membrane proteins via an ester or thioester linkage. Myristoylation and palmitoylation appear to play a significant role in subcellular trafficking of proteins between membrane compartments, as well as in modulating protein-protein interactions.

Fatty acids have two distinct regions, a long hydrophobic, hydrocarbon chain and a carboxylic acid group, which is generally ionized in solution (COO—), extremely hydrophilic and readily forms esters and amides. Natural fatty acids commonly have a chain of four to 28 carbons (usually unbranched and even numbered) and may be saturated or unsaturated. Saturated fatty acids contain no double bonds in the hydrocarbon chain and include lauric acid, myristic acid, palmitic acid, stearic acid, and arachidic acid. Unsaturated fatty acids contain at least one double bond in the hydrocarbon chain and include myristoleic acid, palmitoleic acid, sapienic acid, oleic acid, linoleic acid, α-linoleic acid, arachidonic acid, eicosapentaenoic acid, erucic acid, and docosahexaenoic acid.

Prenylation

Protein prenylation involves the attachment of an isoprenoid lipid, such as a farnesyl or a geranyl-geranyl moiety, to a C-terminal cysteine(s) of the target protein (McTaggert, *Cell Mol Life Sci* 2006, 63:255-67). These reactions are catalysed by farnesyltransferase, geranylgeranyltransferase, and Rab geranylgeranyltransferase. (Magee and Seabra, *Biochem J* 2003, 376:e3-4). Due to the hydrophobic nature of the isoprenoid lipid, most prenylated proteins are associated with a membrane. Most farnesylated proteins are involved in cellular signaling where membrane association is important for function. Isoprenoid lipids are also important for mediating protein-protein binding through specialized prenyl-binding domains.

Post Translational Modifications in Viruses

Many viral proteins are extensively modified with post translational modifications, including, but not limited to glycosylation, acylation, and prenylation. In many instances, these post translational modifications are required for the virus to infect a host cell and/or evade the immune system. Post translational modifications are of particular importance in virology because, in general, viral genomes are small and thus there is heightened pressure for coding frugality. By taking advantage of a host's post translational machinery, viruses can exploit multiple pathways and function with minimal genomes, as a single post translational modification can alter a protein's function or cellular location.

For example, in HIV and Simian Immunodeficiency Viruses (SIV), glycosylation plays an important role during multiple stages of the infectivity cycle. During infection, viral glycoproteins influence the binding of viral proteins gp120 and gp41 to host cell CD4 receptor and CXCR4 and CCR5 co-receptors (Chen et al., *Virus Res* 2001, 79:91-101). Glycosylation is responsible for the proper folding and processing of gp160 (the precursor to gp 120 and gp41 (Land et al., *Biochimie* 2001, 83: 783-90) and can enhance the interactions of HIV and SIV with different cell types, including dendritic cells (Geijtenbeek et al., *Curr Top Microbiol Immunol* 2003, 276:31-54). The normal role of gp120 in HIV biology is to initiate viral binding to cells via CD4 receptor and CXCR4 and CCR5 co-receptors expressed on the target cell. When gp120 engages CD4, conformational changes occur in gp120 that expose co-receptor binding sites and trigger conformational changes in gp41. The conformational changes in gp41, in turn, expose a fusion peptide in gp41, that mediates fusion between the viral envelope and the target cell (Chen et al., *Virus Res* 2001, 79:91-101). The change of one carbohydrate at a single residue (N197) in gp120 completely changes viral tropism from CD4 tropic to CD4 independent (Kolchinksy et al., *J Virol* 2001, 75:3435-43). Changing the overall ratios of high mannose in comparison to complex type carbohydrates (sialic acid containing) present in gp120 affects the degree of viral binding to target cells (Fenouillet et al., *J Gen Virol* 1991, 1919-26). Following infection, glycosylation is required for cleavage of the envelope precursor protein (gp160) into gp120 and gp41. Upon release of the virus from an infected cell, glycosylation is also important for immune evasion as changes in envelope glycosylation significantly alter humoral immune responses to virus (Kwong et al., *Nature* 2002, 420:678-82; Shi et al., *J Gen Virol* 2005, 86:3385-96).

The acylation of viral proteins is also important to HIV biology. HIV budding is a complex process involving the coordination of many cellular and viral proteins (Resh *Trends Microbiol* 2001, 9:57; Freed, *J Virol* 2002, 76:4679-87). HIV budding is directed to an area of the plasma membrane enriched in membrane rafts (Lindwasser et al., *J Virol* 2001, 75:7913-24; Nguyen et al., *J Virol* 2000, 74:3264-72; Ono et al., *Proc Natl Acad Sci USA* 2001, 98:13925-30; Hermida-Matsumoto et al., *J Virol* 2000, 74:8670-79), previously called lipid rafts (Pike et al., *J Lipid Res* 2006, 47:1597-98) by myristoylation of the N-terminal glycine of the capsid protein polyprotein precursor (pr55 gag) (Lindwasser et al., *J Virol* 2001, 75:7913-24; Nguyen et al., *J Virol* 2000, 74:3264-72; Ono et al., *Proc Natl Acad Sci USA* 2001, 98:13925-30). The gp120 protein is directed to membrane rafts by palmitoylation (Yang et al., *Proc Natl Acad Sci USA* 1995, 92:9871-75). Membrane rafts play an important role in several cellular processes including endocytosis, vesicle transport, cholesterol sorting, apoptosis, and signaling through the T cell receptor (Jordan et al., *J Immunol* 2003, 171:78-87; Viola et al., *Apmis* 1999, 107: 615-23; Viola et al., *Science* 1999, 283:680-82; Bezombes et al., *Curr Med Chem Anti-Canc Agents* 2002, 3:263-70; Kabouridis et al., *Eur J Immunol* 2000, 30:954-63). Direction of HIV proteins to these regions may allow the virions to more efficiently hijack these pathways, thus potentially explaining the complex pathogenicity associated with disease progression in AIDS. In fact, the removal of cholesterol, an important membrane raft component, from HIV particles results in inactivation by at least two mechanisms, a loss of the ability to fuse to the target cell and the loss of virion integrity resulting in permeabilization of the virus (Guyader et al, *J Virol* 2002, 76:10356-64; Campbell et al., *J Virol* 2004, 78:10556-65; Viard et al., *J Virol* 2002, 76:11584-595; Campbell et al., *Aids* 2002, 16:2253-61; Liao et al, *AIDS Res Hum Retroviruses* 2003, 19:675-87; Graham et al., *J Virol* 2003, 77:8237-48).

Viruses can also use the host cell machinery to modify viral proteins by adding isoprenoid lipids, such as the farnesyl and geranylgeranyl groups. For example, prenylation plays an important role in the life cycle of the hepatitis delta virus (HDV), the etiologic agent of acute and chronic liver disease associated with hepatitis B virus. (Einav and Glenn, *J Antimicrobial Chemotherapy* 2003, 52:883-86). One of the HDV proteins, the large delta antigen (LHDAg), is critical for viral assembly and undergoes farnesylation in both in vitro translation systems and in intact cells. (Einav and Glenn, *J Antimicrobial Chemotherapy* 2003, 52:883-86). Inhibiting prenylation by using farnesyltransferase inhibitors prevents HDV assembly and clears HDV viremia in a mouse model of HDV, thus underscoring the importance of prenylation in the life cycle of certain viruses. (Einav and Glenn, *J Antimicrobial Chemotherapy* 2003, 52:883-86).

Similar to HIV, SIV, and HDV, other viruses rely on post translational modifications of viral proteins to mediate entry into host cells and/or to evade the host immune system. Thus, the azide-modified fatty acids, azide-modified carbohydrates, and azide-modified isoprenoid lipids described herein are expected to have a broad range of anti-viral activity (such as modulating activity by inhibiting or preventing reverse transcription of the HIV viral genome, late-stage processing of certain viral proteins prior to final assembly of new virons, or viral entry into the cell) and can be used to treat a wide variety of viral infections.

Methods of Use

1. Method of Treating a Viral Infection

The present disclosure provides a method of treating a plant, insect or an animal infected with a virus, the method comprising administering to the plant, insect or animal an effective amount of an azide-modified fatty acid, an azide-modified carbohydrate, or an azide-modified isoprenoid lipid. In one embodiment, the azide-modified fatty acid is a saturated fatty acid, such as 15-azidopentadecanoic acid or 12-azidododecanoic acid. In another embodiment, the azide-modified carbohydrate is an N-linked carbohydrate or an O-linked carbohydrate. In yet another embodiment, the azide-modified carbohydrate is N-azidoacetylgalactosamine, N-azidoacetyl-D-mannosamine, or N-azido-acetylglucosamine. The azide-modified carbohydrate optionally comprises a moiety that facilitates entry into the cell including, but not limited to, a tetraacetyl moiety. Thus, in another embodiment, the azide-modified carbohydrate is tetraacetylated N-azidoacetylgalactosamine, tetraacetylated N-azidoacetyl-D-mannosamine, or tetraacetylated N-azido-acetylglucosamine. In another embodiment, the isoprenoid lipid comprises a farnesyl group or a geranylgeranyl group and includes, but is not limited to, an azido farnesyl diphosphate, an azido farnesyl alcohol, an azido geranylgeranyl diphosphate, or an azido geranylgeranyl alcohol.

The virus may be a plant virus, an insect virus, or an animal virus. In certain embodiments, the animal is a human and the virus is a human virus, such as an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus. In one embodiment, the animal is a human and the virus is a human immunodeficiency virus. Preferably the human immunodeficiency virus is HIV-1.

Whether the azide-modified fatty acid, azide-modified carbohydrate, or azide-modified isoprenoid lipid is effective to treat a viral infection can be determined using any of a variety of assays known in the art. For example, existing animal models or in vitro models of viral infection can be used to determine whether a given compound is effective to reduce viral load. For HIV, by way of example, the in vitro, luciferase reporter assay described in Example 2, can be used to measure the efficacy of an azide-modified compound. In a human subject, the compound's efficacy can be determined by measuring viral load and/or measuring one or more symptoms of a viral infection. Viral load can be measured by measuring the titer or level of virus in serum. These methods include, but are not limited to, a quantitative polymerase chain reaction (PCR) and a branched DNA (bDNA) test.

2. Method of Inhibiting Infectivity of a Virus

Also provided is a method of inhibiting the infectivity of a virus, the method comprising contacting a cell infected with the virus with an azide-modified fatty acid, an azide-modified carbohydrate, or an azide-modified isoprenoid lipid in an amount effective to inhibit the infectivity of the virus. In one embodiment, the azide-modified fatty acid is a saturated fatty acid, such as 15-azidopentadecanoic acid or 12-azidododecanoic acid. In another embodiment, the azide-modified carbohydrate is an N-linked carbohydrate or an O-linked carbohydrate. In yet another embodiment, the azide-modified carbohydrate is N-azidoacetylgalactosamine, N-azidoacetyl-D-mannosamine, or N-azido-acetylglucosamine. The azide-modified carbohydrate optionally comprises a moiety that facilitates entry into the cell including, but not limited to, a tetraacetyl moiety. Thus, in another embodiment, the azide-modified carbohydrate is tetraacetylated N-azidoacetylgalactosamine, tetraacetylated N-azidoacetyl-D-mannosamine, or tetraacetylated N-azido-acetylglucosamine. In another embodiment, the isoprenoid lipid comprises a farnesyl group or a geranylgeranyl group and includes, but is not limited to, an azido farnesyl diphosphate, an azido farnesyl alcohol, an azido geranylgeranyl diphosphate, or an azido geranylgeranyl alcohol.

The virus may be a plant virus, an insect virus, or an animal virus. In certain embodiments, the cell is a human cell and the virus is a human virus, such as an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus. In one embodiment, the animal is a human and the virus is a human immunodeficiency virus. Preferably the human immunodeficiency virus is HIV-1.

Whether the azide-modified fatty acid, azide-modified carbohydrate, or azide-modified isoprenoid lipid is effective to inhibit the infectivity of a virus can be determined using any of a variety of assays known in the art, including a reporter gene assay, such as the luciferase assay described in Example 2.

3. Method of Labeling a Viral Protein

An azide-modified fatty acid can also be used to label viral proteins that are modified with lipids by post-translational acylation including, but not limited to, palmitoylation and myristoylation. In such post-translational modifications, an azide-modified fatty acid is used to label a viral protein. If desired, the azide labeled viral protein can be coupled to an alkyne labeled reporter molecule using a click chemistry reaction to permit detection of the azide labeled viral protein.

Similarly, an azide-modified carbohydrate can be used to label viral proteins that are modified with carbohydrates by post-translational glycosylation including, but not limited to, N-linked glycosylation and O-linked glycosylation. In such post-translational modifications, an azide-modified carbohydrate is used to label a viral protein. If desired, the azide labeled viral protein can be coupled to an alkyne labeled reporter molecule using click chemistry to permit the detection of the azide labeled viral protein.

An azide-modified isoprenoid lipid can likewise be used to label viral proteins that are modified with lipids by post-translational prenylation including, but not limited to, farnesylation and geranylgeranylation. In such post-translational modifications, an azide-modified isoprenoid lipid is used to label a viral protein. If desired, the azide labeled viral protein can be coupled to an alkyne labeled reporter molecule using a click chemistry reaction to permit detection of the azide labeled viral protein.

Any virus labeled as described above may be coupled to an alkyne labeled reporter molecule or carrier molecule. The term "alkyne" includes, but is not limited to, terminal alkynes and internal alkynes, such as, for example, cyclooctynes and difluorocyclooctynes as described by Agard et al., *J. Am. Chem. Soc.,* 2004, 126 (46):15046-15047, dibenzocyclooctynes as described by Boon et al., WO2009/067663 A1 (2009), and aza-dibenzocyclooctynes as described by Debets et al., Chem. Comm., 2010, 46:97-99. Reporter molecules used in the methods and compositions described herein can contain, but are not limited to, a chromophore, a fluorophore, a fluorescent protein, a phosphorescent dye, a tandem dye, a nanocrystal particle, a hapten, an enzyme and a radioisotope. In certain embodiments, such reporter molecules include fluorophores, fluorescent proteins, haptens, and enzymes.

The azide labeled virus can used to track viral infectivity in vivo whereby the virus labeled with an azide-modified carbohydrate, azide-modified fatty acid, or azide-modified isoprenoid lipid is used to infect cultured cells or a subject. Cells can be infected over a time course then fixed, permeabilized, and click-labeled with a fluorescent alkyne dye. The intracellular location (or transport over a time course) of the fluorescent viral particles can be visualized, for example, by microscopy. Similarly, treatment of small animals with azide-labeled virus can be performed and used to track virus bioavalability in different tissues including detection of the virus in circulating white blood cells by flow cytometry and cell/tissue section microscopy. In some embodiments, the method of tracking a virus in vivo comprises the steps of contacting cultured cells or a subject with an azide-modified carbohydrate, azide-modified fatty acid, azide-modified isoprenoid lipid or a pharmaceutically acceptable salt thereof; contacting the cultured cells or the subject with an alkyne labeled reporter molecule; and tracking the reporter-labeled virus in the cultured cells or the subject. In some embodiments, the method of tracking a virus in vivo comprises the steps of contacting cultured cells or a subject with an azide-modified fatty acid or pharmaceutically acceptable salt thereof; contacting the cultured cells or the subject with an alkyne labeled reporter molecule; and tracking the reporter-labeled virus in the cultured cells or the subject.

Thus, another aspect of the disclosure is directed to a method of producing a human immunodeficiency virus labeled with an azide-modified fatty acid, an azide-modified carbohydrate, or an azide-modified isoprenoid lipid, the method comprising contacting a cell infected with the human immunodeficiency virus with the azide-modified fatty acid, the azide-modified carbohydrate, or the azide-modified isoprenoid lipid so that the azide-modified fatty acid, the azide-modified carbohydrate, or the azide-modified isoprenoid lipid enters the cell and is incorporated into a protein of the virus, thereby producing the labeled virus. In one embodiment, the azide-modified fatty acid is a saturated fatty acid, such as 15-azidopentadecanoic acid or 12-azidododecanoic acid. In another embodiment, the azide-modified carbohydrate is an N-linked carbohydrate or an O-linked carbohydrate. In yet another embodiment, the azide-modified carbohydrate is N-azidoacetylgalactosamine, N-azidoacetyl-D-mannosamine, or N-azidoacetylglucosamine. In another embodiment, the isoprenoid lipid comprises a farnesyl group or a geranylgeranyl group and includes, but is not limited to, an azido farnesyl diphosphate, an azido farnesyl alcohol, an azido geranylgeranyl diphosphate, or an azido geranylgeranyl alcohol. The azide-modified carbohydrate optionally comprises a moiety that facilitates entry into the cell including, but not limited to, a tetraacetyl moiety. Thus, in another embodiment, the azide-modified carbohydrate is tetraacetylated N-azidoacetylgalactosamine, tetraacetylated N-azidoacetyl-D-mannosamine, or tetraacetylated N-azidoacetylglucosamine. In certain embodiments, the cell is a human cell.

Viruses

The azide-modified fatty acids, azide-modified carbohydrates, or azide-modified isoprenoid lipids preferably target post translational modifications common to most viruses and thus represent a new class of anti-viral agents with potential for anti-viral activity against a broad spectrum of viruses. In principle, these compounds may be used to treat a plant, insect or an animal infected with any virus. In some embodiments, the virus is a plant virus. In some embodiments, the virus is an insect virus. In other embodiments, the virus is an animal virus. In yet other embodiments, the virus is a human virus. In one embodiment, the virus is one that infects a non-human mammal, such as a mammalian livestock animal, including, but not limited to, a cow, a horse, a pig, a goat, or a sheep.

In other embodiments, the virus is a DNA virus. DNA viruses include, but are not limited to a virus belonging to one of the following families: adenovirus, astrovirus, hepadnavirus, herpesvirus, papovavirus, and poxvirus. In other embodiments, the virus is an RNA virus. RNA viruses include but are not limited to a virus belonging to one the following families: arenavirus, bunyavirus, calcivirus, coronavirus, filovirus, flavivirus, orthomyxovirus, paramyxovirus, picornavirus, reovirus, retrovirus, rhabdovirus, and togavirus.

1. Non-Human Animal Viruses

In methods directed to treating a viral infection or inhibiting viral infectivity in a non-human animal, the animal virus is preferably selected from a picornavirus, such as a bovine enterovirus, a porcine enterovrus B, a foot-and-mouth disease virus, an equine rhinitis A virus, a bovine rhinitis B virus, a ljungan virus, equine rhinitis B virus, an aichi virus, a bovine kobuvirus, a porcine teschovirus, a porcine sapelovirus, a simian sapelovirus, an avian sapelovirus, an avian encephalomyelitis virus, a duck hepatitis A virus, or a simian enterovirus A; a pestivirus, such as border disease virus, a bovine virus diarrhea, or a classical swine fever virus; an arterivirus, such as an equine arteritis virus, a porcine reproductive and respiratory syndrome virus, a lactate dehydrogenase elevating virus, or a simian haemorrhagic fever virus; a coronavirus, such as a bovine coronavirus, a porcine coronavirus, a feline coronavirus, or a canine coronavirus; a paramyxovirus, such as a hendra virus, a nipah virus, a canine distemper virus, a rinderpest virus, a Newcastle disease virus, and a bovine respiratory syncytial virus; an orthomyxovirus, such as an influenza A virus, an influenza B virus, or an influenza C virus; a reovirus, such as a bluetongue virus; a porcine circovirus, a herpesvirus, such as a pseudorabies virus or a bovine herpesvirus 1; an asfarvirus, such as an African swine fever virus; a retrovirus, such as a simian immunodeficiency virus, a feline immunodeficiency virus, a bovine immunodeficiency virus, a bovine leukemia virus, a feline leukemia virus, a Jaagsiekte sheep retrovirus, or a caprine arthritis encephalitis virus; a flavivirus, such as a yellow fever virus, a West Nile virus, a dengue fever virus, a tick borne encephalitis virus, or a bovine viral diarrhea; or a rhabdovirus, such as a rabies virus.

2. Human Animal Viruses

In methods directed to treating a viral infection or inhibiting viral infectivity in a human, the human virus is preferably selected from an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus.

In preferred embodiments, the adenovirus includes, but is not limited to, a human adenovirus. In preferred embodiments, the astrovirus includes, but is not limited to, a mamastrovirus. In preferred embodiments, the hepadnavirus includes, but is not limited to, the hepatitis B virus. In preferred embodiments, the herpesvirus includes, but is not limited to, a herpes simplex virus type I, a herpes simplex virus type 2, a human cytomegalovirus, an Epstein-Barr virus, a varicella zoster virus, a roseolovirus, and a Kaposi's sarcoma-associated herpesvirus. In preferred embodiments, the papovavirus includes, but is not limited to, human papilloma virus and a human polyoma virus. In preferred embodiments, the poxvirus includes, but is not limited to, a variola virus, a vaccinia virus, a cowpox virus, a monkeypox virus, a smallpox virus, a pseudocowpox virus, a papular stomatitis virus, a tanapox virus, a yaba monkey tumor virus, and a molluscum contagiosum virus. In preferred embodiments, the arenavirus includes, but is not limited to lymphocytic choriomeningitis virus, a lassa virus, a machupo virus, and a junin virus. In preferred embodiments, the bunyavirus includes, but is not limited to, a hanta virus, a nairovirus, an orthobunyavirus, and a phlebovirus. In preferred embodiments, the calcivirus includes, but is not limited to, a vesivirus, a norovirus, such as the Norwalk virus and a sapovirus. In preferred embodiments, the coronavirus includes, but is not limited to, a human coronavirus (etiologic agent of severe acute respiratory syndrome (SARS)). In preferred embodiments, the filovirus includes, but is not limited to, an Ebola virus and a Marburg virus. In preferred embodiments, the flavivirus includes, but is not limited to, a yellow fever virus, a West Nile virus, a dengue fever virus, a hepatitis C virus, a tick borne encephalitis virus, a Japanese encephalitis virus, a Murray Valley encephalitis virus, a St. Louis encephalitis virus, a Russian spring-summer encephalitis virus, a Omsk hemorrhagic fever virus, a bovine viral diarrhea virus, a Kyasanus Forest disease virus, and a Powassan encephalitis virus. In preferred embodiments, the orthomyxovirus includes, but is not limited to, influenza virus type A, influenza virus type B, and influenza virus type C. In preferred embodiments, the paramyxovirus includes, but is not limited to, a parainfluenza virus, a rubula virus (mumps), a morbillivirus (measles), a pneumovirus, such as a human respiratory syncytial virus, and a subacute sclerosing panencephalitis virus. In preferred embodiments, the picornavirus includes, but is not limited to, a poliovirus, a rhinovirus, a coxsackievirus A, a coxsackievirus B, a hepatitis A virus, an echovirus, and an eneterovirus. In preferred embodiments, the reovirus includes, but is not limited to, a Colorado tick fever virus and a rotavirus. In preferred embodiments, the retrovirus includes, but is not limited to, a lentivirus, such as a human immunodeficiency virus, and a human T-lymphotrophic virus (HTLV). In preferred embodiments, the rhabdovirus includes, but is not limited to, a lyssavirus, such as the rabies virus, the vesicular stomatitis virus and the infectious hematopoietic necrosis virus. In preferred embodiments, the togavirus includes, but is not limited to, an alphavirus, such as a Ross river virus, an O'nyong'nyong virus, a Sindbis virus, a Venezuelan equine encephalitis virus, an Eastern equine encephalitis virus, and a Western equine encephalitis virus, and a rubella virus.

3. Plant Viruses

In methods directed to treating a viral infection or inhibiting viral infectivity in a plant, the plant virus is selected from an alfamovirus, an allexivirus, an alphacryptovirus, an anulavirus, an apscaviroid, an aureusvirus, an avenavirus, an aysunviroid, a badnavirus, a begomovirus, a benyvirus, a betacryptovirus, a betaflexiviridae, a bromovirus, a bymovirus, a capillovirus, a carlavirus, a carmovirus, a caulimovirus, a cavemovirus, a cheravirus, a closterovirus, a cocadviroid, a colevirus, a comovirus, a crinivirus, a cucumovirus, a curtovirus, a cytorhabdovirus, a dianthovirus, an enamovirus, an umbravirus & B-type satellite virus, a fabavirus, a fijivirus, a furovirus, a hordeivirus, a hostuviroid, an idaeovirus, an ilarvirus, an ipomovirus, a luteovirus, a machlomovirus, a macluravirus, a marafivirus, a mastrevirus, a nanovirus, a necrovirus, a nepovirus, a nucleorhabdovirus, an oleavirus, an ophiovirus, an oryzavirus, a panicovirus, a pecluvirus, a petuvirus, a phytoreovirus, a polerovirus, a pomovirus, a pospiviroid, a potexvirus, a potyvirus, a reovirus, a rhabdovirus, a rymovirus, a sadwavirus, a SbCMV-like virus, a sequivirus, a sobemovirus, a tenuivirus, a TNsatV-like satellite virus, a tobamovirus, a topocuvirus, a tospovirus, a trichovirus, a tritimovirus, a tungrovirus, a tymovirus, an umbravirus, a varicosavirus, a vitivirus, or a waikavirus.

4. Insect Viruses

In methods directed to labeling an insect virus, treating an insect virus infection, or inhibiting insect viral infectivity, the insect virus is preferably selected from a densovirus, such as Junonia coenia densovirus, Bombyx mori densovirus, Aedes aegypti densovirus, or Periplanta fuliginosa densovirus; an iridovirus, such as iridescent virus 6; a chloriridovirus, a baculovirus, such as nuclear polyhedrosis virus or a granulovirus; a polydnavirus, such as a ichnovirus or a bracovirus; an entomopox virus, such as an entomopox A virus, an entomopox B virus, or an entomopox C virus; an ascovirus, such as a Spodoptera frugiperda ascovirus 1a, a Trichoplusia ni ascovirus 2a, or a Diadromus pulchellus ascovirus 4a; an insect picornavirus, such as a bee acute paralysis virus, a Drosophila P, C, or A virus, a bee virus X virus, or a silkworm flacherie virus; a calicivirus; a nodavirus, such as a black beetle virus, a flock house virus, a nodamura virus, a pariacoto virus, or a gypsy moth virus.

Azide-Modified Biomolecules

The azide-modified biomolecules described herein represent a new class of anti-viral agents. In certain embodiments, the azide-modified biomolecule is a carbohydrate or a pharmaceutically acceptable derivative or prodrug thereof. The carbohydrate can be selected from a wide variety of carbohydrates commercially available and/or widely known to those skilled in the art. In preferred embodiments, the carbohydrate is selected to prevent, inhibit and/or retard viral infection of cells. Preferably the carbohydrate is naturally occurring. It is appreciated that the azide-containing carbohydrate, whether naturally occurring or not, may be modified, for example, by short chain alkylation such as methylation or acetylation, esterification, as well as other derivatizations that maintain antiviral activity.

In one embodiment, the carbohydrate is one that is attached directly or indirectly to a protein through a glycosylation reaction in a cell. In one embodiment, the carbohydrate is an N-linked carbohydrate or an O-linked carbohydrate. In yet another embodiment, the carbohydrate is N-azidoacetylgalactosamine, N-azidoacetyl-D-mannosamine, or N-azidoacetylglucosamine.

In certain embodiments, the azide-modified carbohydrate contains a moiety that facilitates entry into the cell including, but not limited to, a tetraacetyl moiety. Thus, in one embodiment, the azide-modified carbohydrate is a tetraacetylated version of an N-linked carbohydrate or an O-linked carbohydrate. In yet another embodiment, the azide-modified carbohydrate is tetraacetylated N-azidoacetylgalactosamine, tetraacetylated N-azidoacetyl-D-mannosamine, or tetraacetylated N-azidoacetylglucosamine.

In other embodiments, the azide-modified biomolecule is a fatty acid or a pharmaceutically acceptable derivative or prodrug thereof. The fatty acid can be selected from a wide variety of fatty acids commercially available and/or widely known to those skilled in the art. In preferred embodiments, the fatty acid is selected to prevent, inhibit and/or retard viral infection of cells. Preferably, the fatty acid is naturally occurring.

In one embodiment, the fatty acid is saturated or unsaturated and has a hydrocarbon chain with an even number of carbon atoms, such as 4-24 carbon atoms. Suitable unsaturated free fatty acids have a hydrocarbon chain with 14-24 carbon atoms and include palmitoleic acid, oleic acid, linoleic acid, alpha and gamma linolenic acid, arachidonic acid, eicosapentanoic acid and tetracosenoic acid. Suitable saturated fatty acids have a hydrocarbon chain with 4-18 carbon atoms and are preferably selected from butyric or isobutyric acid, succinic acid, caproic acid, adipic acid, caprylic acid, capric acid, lauric acid, myristic acid, palmitic acid stearic acid, and arachidic acid. It is appreciated that the azide-containing fatty acid, whether naturally occurring or not, may be modified by chemical substitution including, but not limited to, short chain alkylation such as methylation or acetylation, esterification, as well as other derivitisations that maintain antiviral activity. In addition, it is possible to replace the fatty acid in the azide-modified biomolecule with an alkyne, ketone, or other small molecule that has been shown to be metabolically compatible.

In some embodiments, azide-modified fatty acid or pharmaceutically acceptable salt thereof, has the formula: Y—$CH_2$—X—$CO_2$H, wherein, Y is H or an azido group; and when Y is an azido group, X is a linear or branched carbon chain comprising 6 to 28 carbons, wherein one or more of said carbons may be independently replaced by an oxygen, selenium, silicon, sulfur, SO, $SO_2$ or $NR_1$, or wherein one or more pairs of said carbons adjacent to one another may be attached to one another by a double or triple bond; or when Y is H, X is a linear or branched carbon chain comprising 6 to 28 carbons, wherein one hydrogen on one of said carbons is replaced with an azido group and wherein one or more of said carbons not having an the azido group attached thereto may be independently replaced by an oxygen, selenium, silicon, sulfur, SO, $SO_2$ or $NR_1$, or wherein one or more pairs of said carbons adjacent to one another and not having an azido group may be attached to one another by a double or triple bond; wherein, $R_1$ is H or an alkyl comprising 1 to 6 carbons.

In one embodiment, the fatty acid is one that is attached to a protein through an acylation reaction (e.g., palmitoylation or myristoylation) in a cell. Thus, in one embodiment, the azide-modified fatty acid is a saturated fatty acid, such as 15-azidopentadecanoic acid (palmitic acid, azide) or 12-azidododecanoic acid (myristic acid, azide). The compounds used in the methods of the present invention may be present in the form of pharmaceutically acceptable salts. For use in medicines, the salts of the compounds of the invention refer to non-toxic pharmaceutically acceptable salts.

The pharmaceutically acceptable salts of these compounds include acid addition salts and base addition salts. The term "pharmaceutically acceptable salts" embraces salts commonly used to form alkali metal salts and to form addition salts of free acids or free bases. The nature of the salt is not critical, provided that it is pharmaceutically acceptable.

Suitable pharmaceutically acceptable acid addition salts of these compounds may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid.

Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Suitable pharmaceutically acceptable base addition salts of the disclosed compounds include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine. All of these salts may be prepared by conventional means from the corresponding compound represented by the disclosed compound by treating, for example, the disclosed compounds with the appropriate acid or base. Pharmaceutically acceptable basic/cationic salts also include, the diethanolamine, ammonium, ethanolamine, piperazine and triethanolamine salts.

Such salts can be formed as known to those skilled in the art.

In yet another embodiment, the azide-modified biomolecule is an azide-modified isoprenoid lipid or a pharmaceutically acceptable derivative or prodrug thereof. The isoprenoid lipid can be selected from a wide variety of isoprenoid lipids commercially available and/or widely known to those skilled in the art. In preferred embodiments, the isoprenoid lipid is selected to prevent, inhibit and/or retard viral infection of cells. Preferably, the isoprenoid lipid is naturally occurring. It is appreciated that the azide-containing isoprenoid lipid, whether naturally occurring or not, may be modified, for example, by short chain alkylation such as methylation or acetylation, esterification, as well as other derivatizations that maintain antiviral activity.

In one embodiment, the isoprenoid lipid is one that is attached to a protein through a prenylation reaction in a cell. In one embodiment, the isoprenoid lipid, in the presence of the catalytic activity of a farnesyltransferase or a geranylgeranyltransferase, is attached to a protein in a cell. In another embodiment, the isoprenoid lipid comprises a farnesyl group or a geranylgeranyl group and includes, but is not limited to, an azido farnesyl diphosphate, an azido farnesyl alcohol, an azido geranylgeranyl diphosphate, or an azido geranylgeranyl alcohol. The azide-modified carbohydrates, azide-modified fatty acids, and azide-modified isoprenoid lipids described herein can be prepared using methods known in the art, including those disclosed in U.S. Patent Application Publication No. 20050222427, U.S. Patent Application Publication No. 2007/0249014, and Hang, H. C. et al., *J Am Chem Soc* 2007, 129:2744-45, the disclosures of which are incorporated by reference in their entirety.

Combination Therapy

In one embodiment, a pharmaceutical composition comprising an azide-modified fatty acid, an azide-modified carbohydrate, or an azide-modified isoprenoid lipid and at least one anti-viral agent is administered in combination therapy. The therapy is useful for treating viral infections, including, but not limited to, an HIV infection. The term "in combination" in this context means that the azide-modified fatty acid, azide-modified carbohydrate, or the azide-modified isoprenoid lipid and the anti-viral agent are given substantially contemporaneously, either simultaneously or sequentially. In one embodiment, if given sequentially, at the onset of administration of the second compound, the first of the two compounds is still detectable at effective concentrations at the site of treatment. In another embodiment, if given sequentially, at the onset of administration of the second compound, the first of the two compounds is not detectable at effective concentrations at the site of treatment.

For example, the combination therapy can include an azide-modified fatty acid, an azide-modified carbohydrate, or an azide-modified isoprenoid lipid co-formulated with, and/or co-administered with, at least one additional anti-viral agent. Although specific examples of anti-viral agents are provided, in principle, the azide-modified fatty acid, azide-modified carbohydrate, or an azide-modified isoprenoid lipid can be combined with any pharmaceutical composition useful for treating a viral infection. Such combination therapies may advantageously use lower dosages of the administered therapeutic agents, thus avoiding possible toxicities or complications associated with the various monotherapies. Moreover, the additional anti-viral agents disclosed herein act on pathways or stage of viral infection in addition to or that differ from the pathway stage of viral infection affected by the azide-modified fatty acid, the azide-modified carbohydrate, or the azide-modified isoprenoid lipid, and thus are expected to enhance and/or synergize with the effects of the azide-modified fatty acid, the azide-modified carbohydrate, or the azide-modified isoprenoid lipid. The additional anti-viral agent may include at least one reverse transcriptase inhibitor, a virus protease inhibitor, a viral fusion inhibitor, a viral integrase inhibitor, a glycosidase inhibitor, a viral neuraminidase inhibitor, an M2 protein inhibitor, an amphotericin B, hydroxyurea, α-interferon, β-interferon, γ-interferon, and an antisense oligonucleotide.

The at least one reverse transcriptase inhibitor includes, but is not limited to, one or more nucleoside analogs, such as Zidovudine (AZT), Didanosine (ddI), Zalcitabine (ddC), Stavudine (d4T), Lamivudine (3TC), Abacavir (ABC), Emtricitabine (FTC), Entecavir (INN), Apricitabine (ATC), Atevirapine, ribavirin, acyclovir, famciclovir, valacyclovir, ganciclovir, and valganciclovir; one or more nucleotide analogs, such as Tenofovir (tenofovir disoproxil fumarate), Adefovir (bis-POM PMPA), PMPA, and cidofovir; or one or more non-nucleoside reverse transcriptase inhibitors, such as Efavirenz, Nevirapine, Delavirdine, and Etravirine.

The at least one viral protease inhibitor includes, but is not limited to, tipranavir, darunavir, indinavir, lopinavir, fosamprenavir, atazanavir, saquinavir, ritonavir, indinavir, nelfinavir, and amprenavir.

The at least one viral fusion inhibitor includes, but is not limited to a CD4 antagonist, such as soluble CD4 or an antibody that binds to CD4, such as TNX-355, BMS-806; a CCR5 antagonist, such as SCH-C, SCH-D, UK-427,857, maraviroc, vicriviroc, or an antibody that binds to CCR5, such as PRO-140; a CXCR4 antagonist, such as, AMD3100 or AMD070; or an antagonist of gp41, such as enfuvirtide.

The at least one viral integrase inhibitor includes, but is not limited to, raltegravir.

The at least one glycosidase inhibitor includes, but is not limited to, SC-48334 or MDL-28574.

The at least one viral neuraminidase inhibitor includes, but is not limited to, oseltamivir, peramivir, zanamivir, and laninamivir. Neuraminidase is a protein on the surface of influenza viruses that mediates the virus' release from an infected cell. (Bossart-Whitaker et al., *J Mol Biol,* 1993, 232:1069-83). The influenza virus attaches to the cell membrane using the viral hemagglutinin protein. The hemagglutinin protein binds to sialic acid moieties found on glycoproteins in the host cell's membranes. In order for the virus to be released from the cell, neuraminidase must enzymatically cleave the sialic acid groups from the host glycoproteins. Thus, inhibiting neuraminidase prevents the release of the influenza virus from an infected cell.

The at least one M2 inhibitor includes, but is not limited to, amantadine and rimantidine. M2 is an ion channel protein found in the viral envelope of the influenza virus (Henckel et al., *J Biol Chem,* 1998, 273:6518-24). The M2 protein plays an important role in controlling the uncoating of the influenza virus, leading to the release of the virion contents into the host cell cytoplasm. Blocking M2 inhibits viral replication.

An azide-modified fatty acid, an azide-modified carbohydrate, or an azide-modified isoprenoid lipid disclosed herein can be used in combination with other therapeutic agents to treat specific viral infections as discussed in further detail below.

Non-limiting examples of agents for treating an HIV infection, with which the azide-modified fatty acid, azide-modified carbohydrate, or the azide-modified isoprenoid lipid can be combined include at least one of the following: Zidovudine (AZT), Didanosine (ddI), Zalcitabine (ddC), Stavudine (d4T), Lamivudine (3TC), Abacavir (ABC), Emtricitabine (FTC), Entecavir (INN), Apricitabine (ATC), Tenofovir (tenofovir disoproxil fumarate), Adefovir (bis-POM PMPA) Efavirenz, Nevirapine, Delavirdine, Etravirine, tipranavir, darunavir, indinavir, lopinavir, fosamprenavir, atazanavir, saquinavir, ritonavir, indinavir, nelfinavir, amprenavir, a CD4 antagonist, such as soluble CD4 or an antibody that binds to CD4, such as TNX-355, BMS-806, a CCR5 antagonist, such as SCH-C, SCH-D, UK-427,857, maraviroc, vicriviroc, or an antibody that binds to CCR5, such as PRO-140, a CXCR4 antagonist, such as, AMD3100 or AMD070, or an antagonist of gp41, such as enfuvirtide.

Specific examples of combination therapy that can be used to treat HIV infection include, but are not limited to, an azide-modified fatty acid, azide-modified carbohydrate, or the azide-modified isoprenoid lipid combined with: 1) tenofovir, emtricitabine, and efavirenz; 2) lopinavir and ritonavir; 3) lamivudine and zidovudine; 4) abacavir, lamivudine, and zidovudine; 5) lamivudine and abacavir; or 6) tenofovir and emtricitabine.

Non-limiting examples of agents for a herpesvirus infection with which the azide-modified fatty acid, the azide-modified carbohydrate, or the azide-modified isoprenoid lipid can be combined include acyclovir, famciclovir, valacyclovir, cidofovir, foscarnet, ganciclovir, and valganciclovir.

Non-limiting examples of agents for an influeneza virus infection with which the azide-modified fatty acid, the azide-modified carbohydrate, or the azide-modified isoprenoid lipid can be combined include amantadine, rimantidine, oseltamivir, peramivir, zanamivir, and laninamivir.

Non-limiting examples of agents for a respiratory synctial virus infection with which the azide-modified fatty acid, the azide-modified carbohydrate, or the azide-modified isoprenoid lipid can be combined include ribavirin.

Another aspect of the present invention accordingly relates to kits for carrying out the combined administration of the azide-modified fatty acid, the azide-modified carbohydrate, or the azide-modified isoprenoid lipid with other therapeutic agents. In one embodiment, the kit comprises the azide-modified fatty acid, the azide-modified carbohydrate, or the azide-modified isoprenoid lipid formulated in a pharmaceutical excipient, and at least one anti-viral agent, formulated as appropriate in one or more separate pharmaceutical preparations.

Pharmaceutical Compositions and Methods of Administration

This disclosure provides compositions that are suitable for pharmaceutical use and administration to patients. The pharmaceutical compositions comprise an azide-modified fatty acid, an azide-modified carbohydrate, an azide-modified isoprenoid lipid or any of the compounds herein and a pharmaceutically acceptable excipient. In one embodiment, the azide-modified fatty acid is a saturated fatty acid, such as 15-azidopentadecanoic acid or 12-azidododecanoic acid. In another embodiment, the azide-modified carbohydrate is an N-linked carbohydrate or an O-linked carbohydrate. In yet another embodiment, the azide-modified carbohydrate is N-azidoacetylgalactosamine, N-azidoacetyl-D-mannosamine, or N-azidoacetylglucosamine. In another embodiment, the azide-modified carbohydrate contains a moiety that facilitates entry into the cell including, but not limited to, a tetraacetyl moiety. Thus, in one embodiment, the azide-modified carbohydrate is a tetraacetylated version of an N-linked carbohydrate or an O-linked carbohydrate. In yet another embodiment, the azide-modified carbohydrate is tetraacetylated N-azidoacetylgalactosamine, tetraacetylated N-azidoacetyl-D-mannosamine, or tetraacetylated N-azidoacetylglucosamine. In another embodiment, the isoprenoid lipid comprises a farnesyl or a geranylgeranyl group and includes, but is not limited to, an azido farnesyl diphosphate, an azido farnesyl alcohol, an azido geranylgeranyl diphosphate, or an azido geranylgeranyl alcohol. The pharmaceutical compositions may also be included in a container, pack, or dispenser together with instructions for administration.

A pharmaceutical composition is formulated to be compatible with its intended route of administration. Methods to accomplish the administration are known to those of ordinary skill in the art. Pharmaceutical compositions may be topically or orally administered, or capable of transmission across mucous membranes. Examples of administration of a pharmaceutical composition include oral ingestion or inhalation. Administration may also be intravenous, intraperitoneal, intramuscular, intracavity, subcutaneous, cutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, Cremophor EL™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin.

Oral compositions include an inert diluent or edible carrier. The composition can be enclosed in gelatin or compressed into tablets. For the purpose of oral administration, the azide-modified fatty acid, the azide-modified carbohydrate, or the azide-modified isoprenoid lipid can be incorporated with excipients and placed in tablets, troches, or capsules. Pharmaceutically compatible binding agents or adjuvant materials can be included in the composition. The tablets, troches, and capsules, may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; or (6) a sweetening agent or a flavoring agent.

The composition may also be administered by a transmucosal or transdermal route. Transmucosal administration can be accomplished through the use of lozenges, nasal sprays, inhalers, or suppositories. Transdermal administration can also be accomplished through the use of a composition containing ointments, salves, gels, or creams known in the art. For transmucosal or transdermal administration, penetrants appropriate to the barrier to be permeated are used.

For administration by inhalation, the azide-modified fatty acid, the azide-modified carbohydrate, or the azide-modified isoprenoid lipid are delivered in an aerosol spray from a pressured container or dispenser, which contains a propellant (e.g., liquid or gas) or a nebulizer. In certain embodiments, the azide-modified fatty acid, the azide-modified carbohydrate, or the azide-modified isoprenoid lipid is prepared with a carrier to protect the compounds against rapid elimination from the body. Biodegradable polymers (e.g., ethylene vinyl acetate, polyanhydrides, polyglycolic acid, collagen, polyorthoesters, polylactic acid) are often used. Methods for the preparation of such formulations are known by those skilled in the art.

In other embodiments, the composition comprises a delivery agent for delivering the azide-modified fatty acid, the azide-modified carbohydrate, or the azide-modified isoprenoid lipid to a cell including but not limited to, a liposome. Liposomes (also known as lipid vesicles) are colloidal particles that are prepared from polar lipid molecules derived either from natural sources or chemical synthesis. Such spherical, closed structures composed of curved lipid bilayers, are typically used to entrap drugs, which are often cytotoxic, in order to reduce toxicity and/or increase efficacy. Liposome-entrapped drug preparations are often provided in a dry (e.g. freeze-dried) form, which is subsequently reconstituted with an aqueous solution immediately prior to administration. This is done in order to minimize the possibility of leakage of e.g. cytotoxic drug into aqueous solution and thereby reducing the entrapping effect of the liposome.

Examples of formulations comprising inter alia liposome-encapsulated active ingredients are discussed in U.S. Pat. Nos. 4,427,649, 4,522,811, 4,839,175, 5,569,464, EP 249 561, WO 00/38681, WO 88/01862, WO 98/58629, WO 98/00111, WO 03/105805, U.S. Pat. Nos. 5,049,388, 5,141, 674, 5,498,420, 5,422,120, WO 87/01586, WO 2005/039533, US 2005/0112199 and U.S. Pat. No. 6,228,393, all of which are hereby incorporated by reference in their entirety.

The azide-modified fatty acid, azide-modified carbohydrate, or azide-modified isoprenoid lipid containing compositions are administered in therapeutically effective amounts as described. Therapeutically effective amounts may vary with the subject's age, condition, sex, and severity of medical condition. Appropriate dosage may be determined by a physician based on clinical indications. The azide-modified fatty acid, azide-modified carbohydrate, or azide-modified isoprenoid lipid containing composition may be given as a bolus dose to maximize the circulating levels of the azide-modified fatty acid, azide-modified carbohydrate, or the azide-modified isoprenoid lipid for the greatest length of time. Continuous infusion may also be used after the bolus dose.

Examples of dosage ranges that can be administered to a subject can be chosen from: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject characteristics. Dosages can also be administered via continuous infusion (such as through a pump). The administered dose may also depend on the route of administration. For example, subcutaneous administration may require a higher dosage than intravenous administration.

In certain circumstances, it may be advantageous to formulate compositions in dosage unit form for ease of administration and uniformity of dosage. Dosage unit form as used herein refers to physically discrete units suited for the patient. Each dosage unit contains a predetermined quantity of azide-modified fatty acid, the azide-modified carbohydrate, or the azide-modified isoprenoid lipid calculated to produce a therapeutic effect in association with the carrier. The dosage unit depends on the characteristics of the azide-modified fatty acid, the azide-modified carbohydrate, or the azide-modified isoprenoid lipid and the particular therapeutic effect to be achieved.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used to formulate a dosage range in humans. The dosage of these compounds may lie within the range of circulating concentrations of the azide-modified fatty acid, azide-modified carbohydrate, or azide-modified isoprenoid lipid in the blood, that includes an $ED_{50}$ with little or no toxicity. The dosage may vary within this range depending upon the dosage composition form employed and the route of administration. For any azide-modified fatty acid, azide-modified carbohydrate, or azide-modified isoprenoid lipid used in the methods described herein, the therapeutically effective dose can be estimated initially using cell culture assays. A dose may be formulated in animal models to achieve a circulating plasma concentration range that includes the $IC_{50}$ (i.e., the concentration of antibody which achieves a half-maximal inhibition of symptoms). The effects of any particular dosage can be monitored by a suitable bioassay.

The compositions may also contain other active compounds providing supplemental, additional, or enhanced therapeutic functions. In one embodiment, the composition further comprises at least one anti-viral agent, such as a reverse transcriptase inhibitor, a virus protease inhibitor, a viral fusion inhibitor, a viral integrase inhibitor, a glycosidase inhibitor, an amphotericin B, hydroxyurea, α-interferon, β-interferon, γ-interferon, and an antisense oligonucleotide.

In one embodiment, the at least one reverse transcriptase inhibitor includes, but is not limited to, one or more nucleoside analogs, such as Zidovudine (AZT), Didanosine (ddI), Zalcitabine (ddC), Stavudine (d4T), Lamivudine (3TC), Abacavir (ABC), Emtricitabine (FTC), Entecavir (INN), Apricitabine (ATC), Atevirapine, ribavirin, acyclovir, famciclovir, valacyclovir, ganciclovir, and valganciclovir; one or more nucleotide analogs, such as Tenofovir (tenofovir disoproxil fumarate), Adefovir (bis-POM PMPA), PMPA, and cidofovir; or one or more non-nucleoside reverse transcriptase inhibitors, such as Efavirenz, Nevirapine, Delavirdine, and Etravirine.

In other embodiments, the at least one viral protease inhibitor includes, but is not limited to, tipranavir, darunavir, indinavir, lopinavir, fosamprenavir, atazanavir, saquinavir, ritonavir, indinavir, nelfinavir, and amprenavir.

In other embodiments, the at least one viral fusion inhibitor includes, but is not limited to a CD4 antagonist, such as soluble CD4 or an antibody that binds to CD4, such as TNX-355, BMS-806; a CCR5 antagonist, such as SCH-C, SCH-D, UK-427,857, maraviroc, vicriviroc, or an antibody that binds to CCR5, such as PRO-140; a CXCR4 antagonist, such as, AMD3100 or AMD070; or an antagonist of gp41, such as enfuvirtide.

In other embodiments, the at least one viral integrase inhibitor includes, but is not limited to, raltegravir.

In other embodiments, the at least one glycosidase inhibitor includes, but is not limited to, SC-48334 or MDL-28574.

Reference will now be made in detail to various exemplary embodiments. It is to be understood that the following detailed description is provided to give the reader a fuller understanding of certain embodiments, features, and details of aspects of the invention, and should not be interpreted as a limitation of the scope of the invention.

EXAMPLE 1

Labeling HIV with Azide-Modified Biomolecules

CEMx174 cells were transfected with $HIV_{NL4-3}$ in a T-150 flask and the virus production was monitored by reverse transcriptase activity until peak virus production occurred (usually 7 to 9 days post transfection). Prior to transfection, the CEMx174 cells were spiked with the following azide-modified biomolecules: 15-azidopentadecanoic acid (50-100 µM), 12-azidododecanoic acid (50-100 µM), tetraacetylated N-azidoacetylgalactosamine (20-40 µM), and tetraacetylated N-azidoacetyl-D-mannosamine (20-40 µM).

Infected cells were harvested at 12, 24, 72 hours, and 14 days. Harvested cells were isolated and lysed. Cell lysates were then mixed with the CLICK-IT® detection reagent, tetramethylrhodamine (TAMRA) alkyne and the CLICK-IT® Protein Reaction Buffer Kit (Invitrogen, Carlsbad, Calif.). Cell lysate samples were run on a one-dimensional gel to monitor changes in the azide labeled proteins over time (FIG. 1).

Figure 2:
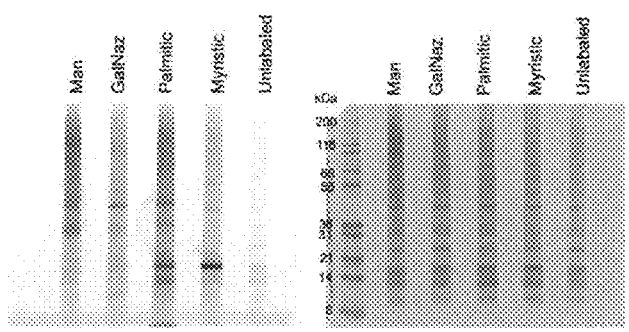
FIG. 2 shows gel electrophoresis of azide-modified proteins from HIV produced from chronically infected CEMx174 cells. The left panel shows viral proteins tagged with tetraacetylated N-azidoacetyl-D-mannosamine (Man), tetraacetylated N-azidoacetylgalactosamine (GalNaz), 15-azidopentadecanoic acid (Palmitic), 12-azidododecanoic acid (Myristic) and labeled with TAMRA. The right panel shows a total protein stain using SYPRO® Ruby protein stain (Sigma-Aldrich, St. Louis, Mo.).

Labeled virus was also obtained from the transfected cells. More specifically, virus-containing supernatants were collected and virus was purified through 20% sucrose as previously described (Graham, D. R. et al., *Proteomics* 2008, 8:4919-30). The purified virus was then mixed with the CLICK-IT® detection reagent, tetramethylrhodamine (TAMRA) alkyne and the CLICK-IT® Protein Reaction Buffer Kit (Invitrogen, Carlsbad, Calif.). Virus samples were run on a one-dimensional gel to reveal azide-labeled viral proteins (FIG. 2). Virus levels were normalized p24 content and by one-dimensional gel electrophoresis.

No apparent effects of acute or chronic replication of HIV on host cellular protein modifications were observed (FIG. 1, compare label to controls). The azide-modified biomolecules, however, did label viral proteins and permit their detection at the expected molecular weights for HIV viral proteins: 55 KDa (gag—myristoylated); 41 KDa (gp41—palmitoylated) and 120 KDa (gp120—N-glycosylated) at 14 days in chronically infected cells (FIG. 1).

EXAMPLE 2

Inhibiting Infectivity of HIV

Figure 3:
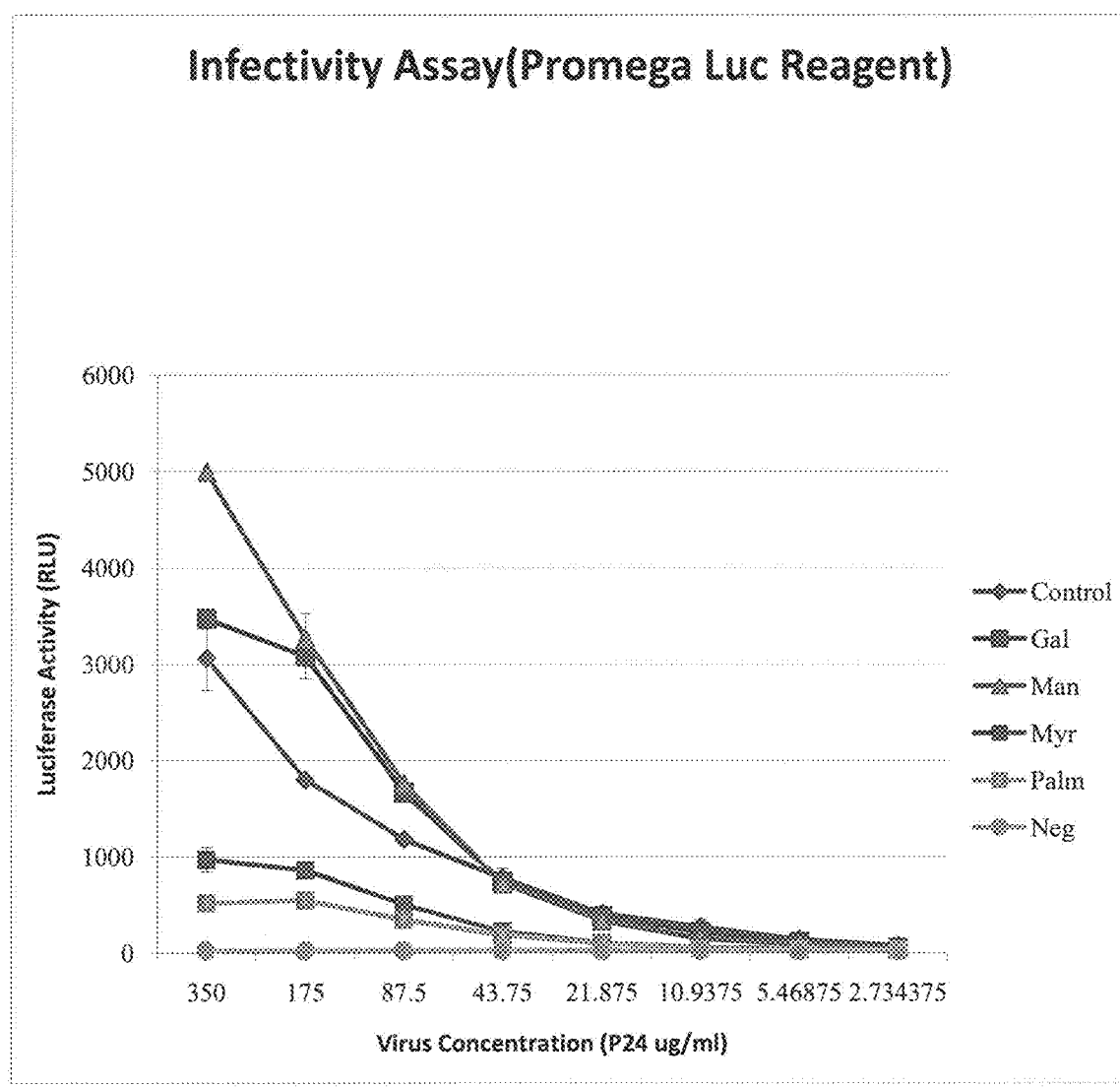
FIG. 3 shows the results of a luciferase reporter assay (Applied Biosytems luciferase reagent) to measure the infectivity of unlabeled HIV (CONTROL) or HIV labeled with 15-azidopentadecanoic acid (PALM), 12-azidododecanoic acid (MYR), tetraacetylated N-azidoacetyl-D-mannosamine (MAN), or tetraacetylated N-azidoacetylgalactosamine (GAL).
Figure 4:
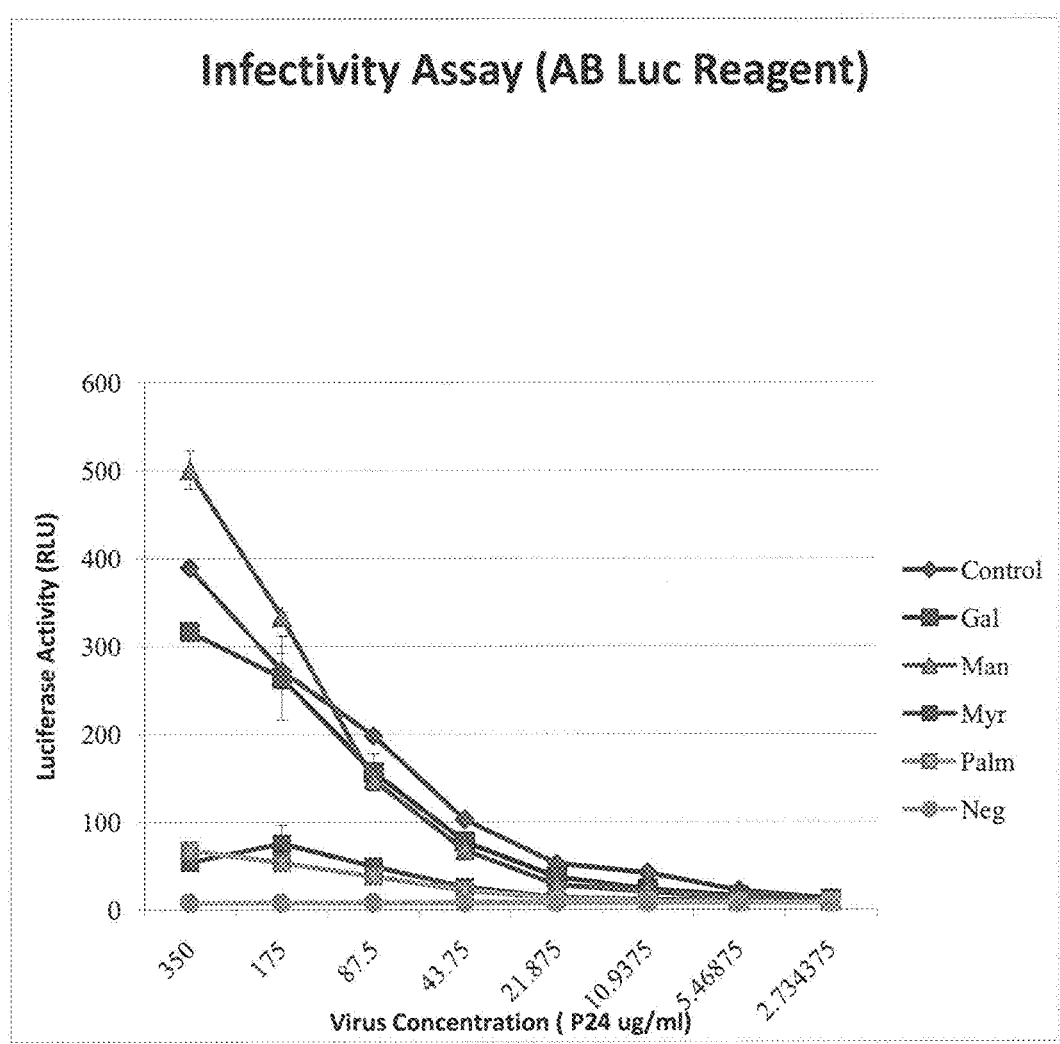
FIG. 4 shows the results of a luciferase reporter assay (Promega luciferase reagent) to measure the infectivity of unlabeled HIV (CONTROL) or HIV labeled with 15-azidopentadecanoic acid (PALM), 12-azidododecanoic acid (MYR), tetraacetylated N-azidoacetyl-D-mannosamine (MAN), or tetraacetylated N-azidoacetylgalactosamine (GAL).

To examine the effect of the azide-modified biomolecules on the innate biology of the virus, the azide-labeled virus from the transfected cells was isolated and tested in cell infection studies. Unlabeled HIV, at a concentration 100 times less than the test samples, was used as a control. Viral loads were normalized to p24 abundance and virus incubated for 12 hours on a reporter cell line (TZM/BI). TZM/BI is a genetically engineered HeLa cell line that expresses CD4, CXCR4 and CCR5 and contains Tat-inducible luciferase and β-Gal reporter genes. Viral infectivity was determined by measuring cellular luciferase activities with two different luciferase reagents. The results using a single cycle replication system showed that virus labeled with the azide-modified biomolecules, particularly 12-azidododecanoic acid, and to a lesser extent, 15-azidopentadecanoic acid and tetraacetylated N-azidoacetylgalactosamine, had a profound impact on the infectivity of the virus (FIGS. 3 and 4). The level of inhibition of viral entry observed was comparable to the level of inhibition observed in cells pre-treated with an anti-retroviral agent, such as a fusion inhibitor or a nucleoside analogue.

EXAMPLE 3

Toxicity Profile

Little to no toxicity has been observed using these azide-modified biomolecules in various eukaryotic cell lines, suggesting that these compounds have minimal toxicity profile and supporting their use in a therapeutic setting.

EXAMPLE 4

Inhibition of Insect Cell Baculovirus Infectivity

Inhibition of insect cell baculovirus infectivity with azido fatty acid analogs: The BacMam system uses a modified insect cell virus (baculovirus) as a vehicle to efficiently deliver and express genes in mammalian cells, A Nuclear-GFP BacMam 2.0 expression system (Invitrogen, C10602) was used as a model to determine if PTM analog labeling of the virus would affect mammalian cell infectivity. Viruses were labeled with various PTM analogs and used to infect mammalian cells. Infectivity was determined by the expression of nuclear-GFP, is viral entry into the cell is required for expression of GFP protein.

Labeling and amplification of Nuclear-GFP BacMam 2.0 Virus: To label, amplify and enrich BacMam viruses with azide/alkyne posttranslational modification (PTM) analogs, 20 ml of Sf9 insect cells at a concentration of 1.5E6 cells/ml in Sf-900 II SFM insect cell media were infected with Nuclear-GFP BacMam 2.0 at a multiplicity of infection (MOI) of 0.1 viruses/cell. Various PTM analogs including palmitic acid azide (15-azidopentadecanoic acid)(Invitrogen, C10265), myristic acid azide (12-azidododecanoic acid)) (Invitrogen, C10268), fucose alkyne (Invitrogen, C10264), ManNAz (tetraacetylated N-azidoacetyl-d-mannosamine) (Invitrogen, C33366), and GalNAz (tetraacetylated N-azidoacetylgalactosamine) (Invitrogen, C33365), in DMSO or 100% ethanol were added to the insect cells at the same time to a final concentration of 50 uM. The cultures were shaken (120 rpm) in the dark at 27C for 4 days. The BacMam baculoviruses were harvested by centrifugation at 1000×g, 15 for minutes. The resulting supernatants were filtered through a 0.22 um sterile filter into separate sterile, amber, 50 ml conical vials and stored at 4C.

Characterization of BacMam virus production: To verify, quantitate, and normalize the amount of enriched viruses obtained from insect cell supernatants, samples of each virus were lysed in SDS sample preparation buffer (SPB), sonicated with a probe tip sonicator, and heated at 90C to completely dissolve the viral proteins. Viral protein concentrations of the lysates were then determined. Viral lysate samples were separated by 1D SDS-PAGE and then analyzed by Western blot using antibodies against virus specific proteins, gp64 [eBiosciences, mouse monoclonal, 14-69995-85) and VSV-G (Sigma, rabbit polyclonal, V4888)]. Relative virus concentrations obtained from protein analysis and Western blotting were used to normalize virus addition in subsequent viral transduction experiments.

Figure 5:
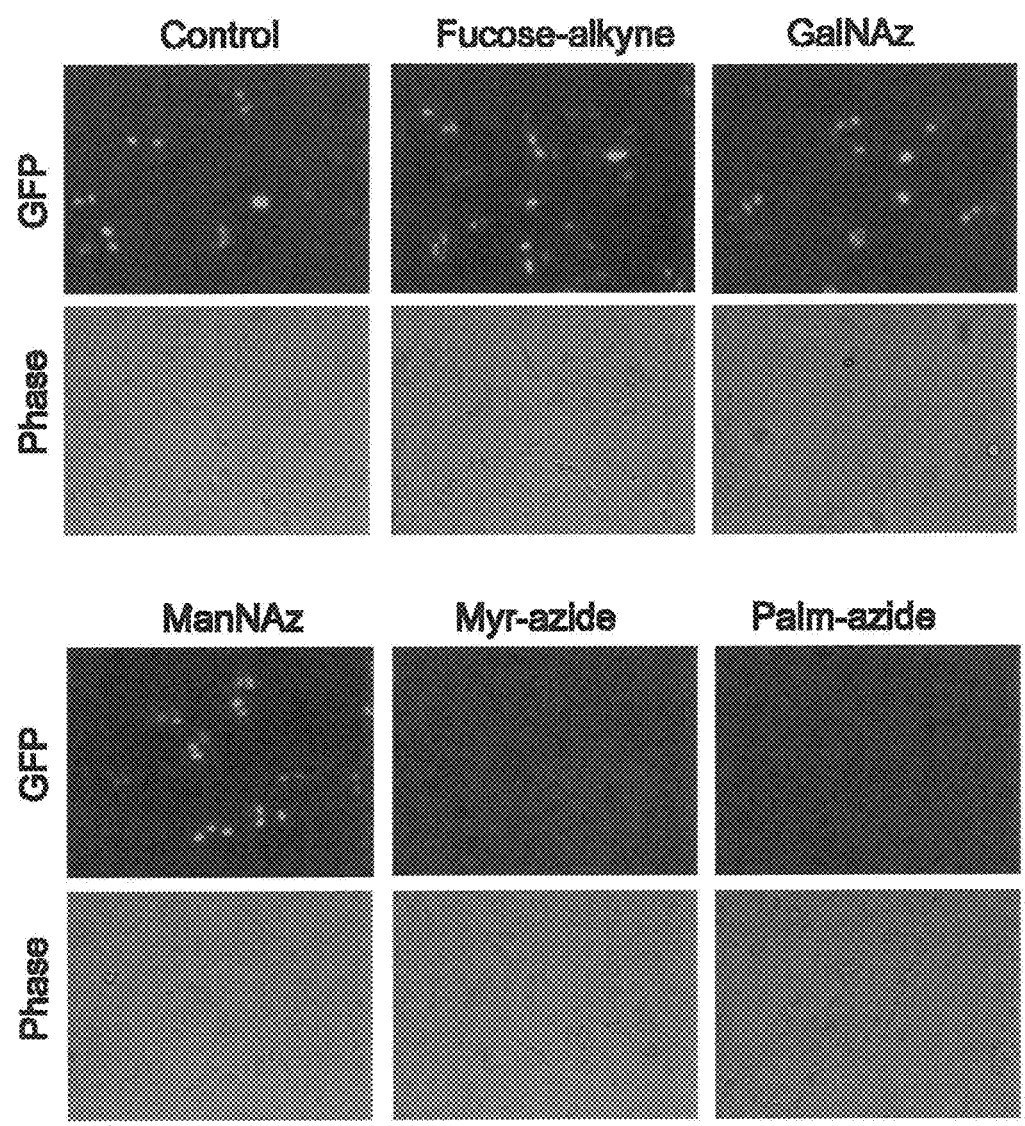
FIG. 5 shows the results of post translational modification (PTM) analog incorporation on the ability of BacMam to enter mammalian cell. The panels show both phase (bottom row of panels) and fluorescent GFP images (top row of panels) of U2-OS cells infected with PTM analog-labeled BacMam viruses.

Mammalian cell infection protocol: To determine if the PTM analog-labeled viruses retain the ability to infect mammalian cells, 50,000 U2-OS cells (human osteosarcoma cell line) were plated onto a 6 well-chamber glass bottom plate. 20 or 50 uL of enriched virus was added into 2 ml final volume of media+serum (McCoy's+10% FBS). The plates were then incubated overnight at 37C, in 5% CO2. The following day cells were imaged on AMG EVOS fluorescence microscope at 10× or 20× magnification using both white light and GFP filters (FIG. 5).

To determine the effect of PTM analog incorporation on the ability of BacMam to enter mammalian cells, a BacMam construct that expresses nuclear GFP was used. As BacMam virus reproduces in insect cells, but not in mammalian cells, sugar and fatty acid analog-labeled viruses were produced in SF9 insect cells, and the labeled viruses were then used to determine infectivity in U2-OS cells (human osteosarcoma cell line). Nuclear GFP expression in U2-OS cells can only take place if the virus is able to enter the cell. The panels of FIG. 5 show both phase (bottom row of panels) and fluorescent GFP images (top row of panels) of U2-OS cells infected with PTM analog-labeled BacMam viruses. In these panels, cells treated with myristate-azide and palmitate-azide labeled viruses showed no nuclear-GFP expression, while control cells (no virus) and cells treated with sugar-labeled viruses show significant nuclear GFP expression.

What is claimed:

1. A method of treating a subject infected with a plant, an insect or an animal virus and in need of treatment for the infection, the method comprising administering to the subject a therapeutically effective amount of an azide-modified carbohydrate or pharmaceutically acceptable salt thereof, wherein the infectivity of the virus is inhibited thereby treating the subject, and wherein the azide-modified carbohydrate is N-azidoacetylgalactosamine, N-azidoacetyl-D-mannosamine, N-azidoacetylglucosamine, tetraacetylated N-azidoacetylgalactosamine or tetraacetylated N-azidoacetylglucosamine.

2. The method of claim 1, wherein the virus is a non-human animal virus or a human animal virus.

3. The method of claim 1, wherein the virus is a plant virus.

4. The method of claim 1, wherein the virus is an insect virus.

5. The method of claim 2, wherein the human animal virus is an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus.

6. The method of claim 5, wherein the retrovirus is a human immunodeficiency virus or a human T-lymphotrophic virus.

7. The method of claim 6, wherein the retrovirus is the human immunodeficiency virus, HIV-1.

8. The method of claim 1, wherein the subject is a human.

* * * * *